US008617819B2

(12) United States Patent
Swager et al.

(10) Patent No.: US 8,617,819 B2
(45) Date of Patent: Dec. 31, 2013

(54) POLYMERS FOR ANALYTE DETECTION

(75) Inventors: Timothy M. Swager, Newton, MA (US); Peter H. Seeberger, Zurich (CH); Juan Zheng, Cambridge, MA (US); Matthew D. Disney, Williamsville, NY (US)

(73) Assignee: Massachusetts Institute of Technology, Cambridge, MA (US)

( * ) Notice: Subject to any disclaimer, the term of this patent is extended or adjusted under 35 U.S.C. 154(b) by 415 days.

(21) Appl. No.: 11/230,308

(22) Filed: Sep. 19, 2005

(65) Prior Publication Data

US 2006/0127929 A1     Jun. 15, 2006

Related U.S. Application Data

(60) Provisional application No. 60/610,743, filed on Sep. 17, 2004.

(51) Int. Cl.
*G01N 33/53* (2006.01)
*G01N 21/76* (2006.01)
*G01N 33/533* (2006.01)

(52) U.S. Cl.
USPC ............................. 435/7.1; 436/172; 436/546

(58) Field of Classification Search
USPC ............ 436/164, 171, 172; 422/82.05, 82.07, 422/82.08
See application file for complete search history.

(56) References Cited

U.S. PATENT DOCUMENTS

| | | |
|---|---|---|
| 3,242,186 A | 3/1966 | Dershowitz |
| 3,785,813 A | 1/1974 | Rickter |

(Continued)

FOREIGN PATENT DOCUMENTS

| | | |
|---|---|---|
| DE | 4121138 | 1/1993 |
| DE | 197 44 792 A1 | 4/1999 |

(Continued)

OTHER PUBLICATIONS

Erdogan et al. Synthesis and mesoscopic order of a sugar-coated poly(p-phenyleneethynylene). Macromolecules, 2002, vol. 35, pp. 7863-7864.*

(Continued)

*Primary Examiner* — Shafiqul Haq
(74) *Attorney, Agent, or Firm* — Wolf, Greenfield & Sacks, P.C.

(57) ABSTRACT

The present invention generally relates to organic polymers able to participate in an analyte-recognition process, where an analyte facilitates an energy transfer between an energy donor and an energy acceptor. Certain embodiments of the invention make use of fluorescent conjugated polymers, such as poly (phenylene ethynylene)s and other polymers comprising pi-conjugated backbones. For example, one aspect of the invention provides a fluorescent conjugated polymer and an indicator that can interact with each other in the presence of an analyte to produce an emissive signal. In some cases, the interaction may include energy exchange mechanisms, such as Dexter energy transfer or the strong coupling effect. The interaction of the conjugated polymer and the indicator, in some instances, may be facilitated through specific interactions, such as a protein/carbohydrate interaction, a ligand/receptor interaction, etc. Another aspect of the invention provides for the detection of biological entities, for example, pathogenic bacteria such as *E. coli*, or viruses such as influenza virus. In some cases, biological recognition elements may be used to determine the biological entity, for instance, carbohydrates that can be used to specifically interact with at least part of the biological entity, such as a protein in the cell membrane of a bacterium. Still other aspects of the invention involve articles, devices, and kits using any of the above-described systems.

13 Claims, 9 Drawing Sheets

(56) References Cited

U.S. PATENT DOCUMENTS

| | | | |
|---|---|---|---|
| 4,049,616 A | 9/1977 | Scott et al. | |
| 4,356,429 A | 10/1982 | Tang | |
| 4,513,078 A | 4/1985 | Sandrik et al. | |
| 4,539,507 A | 9/1985 | VanSlyke et al. | |
| 4,687,732 A | 8/1987 | Ward et al. | |
| 4,839,112 A | 6/1989 | Wynne et al. | |
| 4,841,099 A | 6/1989 | Epstein et al. | |
| 4,868,103 A * | 9/1989 | Stavrianopoulos et al. | 435/5 |
| 4,883,608 A | 11/1989 | Trujillo et al. | |
| 4,894,443 A * | 1/1990 | Greenfield et al. | 424/179.1 |
| 4,927,768 A | 5/1990 | Coughlin et al. | |
| 4,946,890 A | 8/1990 | Meador | |
| 4,957,615 A | 9/1990 | Ushizawa et al. | |
| 4,992,244 A | 2/1991 | Grate | |
| 4,992,302 A | 2/1991 | Lindmayer | |
| 5,091,502 A | 2/1992 | Narang et al. | |
| 5,155,149 A | 10/1992 | Atwater et al. | |
| 5,157,261 A | 10/1992 | Grey et al. | |
| 5,194,393 A | 3/1993 | Hugl et al. | |
| 5,217,715 A * | 6/1993 | Krivan et al. | 435/252.1 |
| 5,236,808 A | 8/1993 | Smothers | |
| 5,237,582 A | 8/1993 | Moses | |
| 5,244,813 A | 9/1993 | Walt et al. | |
| 5,250,439 A | 10/1993 | Musho et al. | |
| 5,254,633 A | 10/1993 | Han et al. | |
| 5,312,896 A | 5/1994 | Bhardwaj et al. | |
| 5,323,309 A | 6/1994 | Taylor et al. | |
| 5,364,797 A | 11/1994 | Olson et al. | |
| 5,387,462 A | 2/1995 | Debe | |
| 5,414,069 A | 5/1995 | Cumming et al. | |
| 5,451,663 A * | 9/1995 | Kang et al. | 530/367 |
| 5,451,683 A | 9/1995 | Barrett et al. | |
| 5,493,017 A | 2/1996 | Therien et al. | |
| 5,511,547 A | 4/1996 | Markle et al. | |
| 5,512,490 A | 4/1996 | Walt et al. | |
| 5,512,635 A | 4/1996 | Nubel et al. | |
| 5,532,129 A * | 7/1996 | Heller | 435/6 |
| 5,540,999 A | 7/1996 | Yamamoto et al. | |
| 5,546,889 A | 8/1996 | Wakita et al. | |
| 5,549,851 A | 8/1996 | Fukushima et al. | |
| 5,554,747 A | 9/1996 | Sharma et al. | |
| 5,556,524 A | 9/1996 | Albers | |
| 5,563,056 A | 10/1996 | Swan et al. | |
| 5,565,322 A | 10/1996 | Heller | |
| 5,580,527 A | 12/1996 | Bell et al. | |
| 5,585,646 A | 12/1996 | Kossovsky et al. | |
| 5,591,787 A | 1/1997 | Schlennert et al. | |
| 5,597,890 A | 1/1997 | Jenekhe | |
| 5,607,864 A | 3/1997 | Ricchiero et al. | |
| 5,629,353 A | 5/1997 | Steckle, Jr. et al. | |
| 5,674,698 A | 10/1997 | Zarling et al. | |
| 5,674,751 A | 10/1997 | Jaduszliwer et al. | |
| 5,675,001 A | 10/1997 | Hoffman et al. | |
| 5,679,773 A | 10/1997 | Holmes | |
| 5,700,696 A | 12/1997 | Chandross et al. | |
| 5,705,348 A | 1/1998 | Meade et al. | |
| 5,709,994 A | 1/1998 | Pease et al. | |
| 5,710,187 A | 1/1998 | Steckle, Jr. et al. | |
| 5,710,197 A | 1/1998 | Fischer et al. | |
| 5,723,218 A | 3/1998 | Haugland et al. | |
| 5,858,907 A | 1/1999 | Wang et al. | |
| 5,869,592 A | 2/1999 | Gagne et al. | |
| 5,925,517 A | 7/1999 | Tyagi et al. | |
| 5,942,638 A | 8/1999 | Lichtenhan et al. | |
| 5,998,204 A * | 12/1999 | Tsien et al. | 435/325 |
| 6,020,426 A | 2/2000 | Yamaguchi et al. | |
| 6,124,421 A | 9/2000 | Lau et al. | |
| 6,254,829 B1 | 7/2001 | Hartmann et al. | |
| 6,259,277 B1 | 7/2001 | Tour et al. | |
| 6,303,733 B1 | 10/2001 | Lau et al. | |
| 6,323,309 B1 | 11/2001 | Swager et al. | |
| 6,328,932 B1 | 12/2001 | Carter et al. | |
| 6,444,476 B1 * | 9/2002 | Morgan | 436/172 |
| 6,444,479 B1 | 9/2002 | Choi | |
| 6,469,123 B1 | 10/2002 | Lau et al. | |
| 6,509,110 B1 | 1/2003 | Salbeck et al. | |
| 6,556,335 B2 | 4/2003 | Lee et al. | |
| 6,589,731 B1 | 7/2003 | Chen et al. | |
| 6,605,693 B1 | 8/2003 | Becker et al. | |
| 6,610,848 B1 | 8/2003 | Pilato et al. | |
| 6,660,820 B1 | 12/2003 | Martin et al. | |
| 6,670,645 B2 | 12/2003 | Grushin et al. | |
| 6,713,298 B2 | 3/2004 | McDevitt et al. | |
| 6,743,640 B2 | 6/2004 | Whitten et al. | |
| 6,770,220 B1 | 8/2004 | Klimant | |
| 6,783,814 B2 | 8/2004 | Swager et al. | |
| 6,828,450 B2 | 12/2004 | Hua et al. | |
| 6,830,828 B2 | 12/2004 | Thompson et al. | |
| 6,835,835 B1 | 12/2004 | Huo | |
| 6,902,830 B2 | 6/2005 | Thompson et al. | |
| 6,919,139 B2 | 7/2005 | Grushin et al. | |
| 6,946,688 B2 | 9/2005 | Grushin et al. | |
| 6,962,757 B2 | 11/2005 | Epstein et al. | |
| 7,001,536 B2 | 2/2006 | Thompson et al. | |
| 7,029,765 B2 | 4/2006 | Kwong et al. | |
| 7,041,910 B2 | 5/2006 | Swager et al. | |
| 7,075,102 B2 | 7/2006 | Grushin et al. | |
| 7,078,725 B2 | 7/2006 | Grushin et al. | |
| 7,087,321 B2 | 8/2006 | Kwong et al. | |
| 7,088,757 B1 | 8/2006 | Yu et al. | |
| 7,098,060 B2 | 8/2006 | Yu et al. | |
| 7,122,383 B2 | 10/2006 | Jones et al. | |
| 7,129,518 B2 | 10/2006 | Grushin et al. | |
| 7,186,355 B2 | 3/2007 | Swager | |
| 7,208,122 B2 | 4/2007 | Swager et al. | |
| 7,250,519 B2 | 7/2007 | Stossel et al. | |
| 7,291,503 B2 | 11/2007 | Swager | |
| 7,393,503 B2 | 7/2008 | Swager et al. | |
| 7,417,146 B2 | 8/2008 | Huo | |
| 7,462,325 B2 * | 12/2008 | Hancock et al. | 422/82.05 |
| 7,521,232 B2 | 4/2009 | Moon | |
| 7,662,309 B2 | 2/2010 | Swager et al. | |
| 7,671,166 B2 | 3/2010 | Swager et al. | |
| 7,759,127 B2 | 7/2010 | Rose et al. | |
| 7,943,062 B2 | 5/2011 | Swager et al. | |
| 8,158,437 B2 | 4/2012 | Swager et al. | |
| 8,198,096 B2 | 6/2012 | Swager et al. | |
| 2002/0040805 A1 | 4/2002 | Swager | |
| 2002/0051985 A1 | 5/2002 | Whitten et al. | |
| 2002/0076830 A1 * | 6/2002 | Mauze et al. | 436/518 |
| 2002/0137978 A1 | 9/2002 | Grubbs et al. | |
| 2002/0150697 A1 | 10/2002 | Swager et al. | |
| 2002/0150759 A1 | 10/2002 | Jones et al. | |
| 2002/0177136 A1 | 11/2002 | McBranch et al. | |
| 2003/0054413 A1 | 3/2003 | Kumaraswamy et al. | |
| 2003/0096138 A1 | 5/2003 | Lecloux et al. | |
| 2003/0134959 A1 | 7/2003 | Hancock et al. | |
| 2003/0178607 A1 | 9/2003 | Swager et al. | |
| 2004/0043251 A1 | 3/2004 | Epstein et al. | |
| 2004/0089867 A1 | 5/2004 | Grushin et al. | |
| 2004/0094768 A1 | 5/2004 | Yu et al. | |
| 2004/0094769 A1 | 5/2004 | Grushin et al. | |
| 2004/0106741 A1 | 6/2004 | Kriesel et al. | |
| 2004/0116650 A1 | 6/2004 | Swager et al. | |
| 2004/0121337 A1 | 6/2004 | Deans et al. | |
| 2004/0170775 A1 | 9/2004 | Swager et al. | |
| 2004/0175768 A1 | 9/2004 | Kushon et al. | |
| 2004/0188673 A1 | 9/2004 | Grushin et al. | |
| 2004/0197602 A1 | 10/2004 | Dobbs et al. | |
| 2004/0235184 A1 | 11/2004 | Swager | |
| 2004/0241768 A1 | 12/2004 | Whitten et al. | |
| 2004/0254388 A1 | 12/2004 | Spreitzer et al. | |
| 2005/0014160 A1 | 1/2005 | Kumaraswamy et al. | |
| 2005/0037232 A1 | 2/2005 | Tyan et al. | |
| 2005/0054854 A1 | 3/2005 | Stossel et al. | |
| 2005/0059168 A1 | 3/2005 | Bazan et al. | |
| 2005/0147534 A1 | 7/2005 | Swager et al. | |
| 2005/0157261 A1 | 7/2005 | Hanebuchi et al. | |
| 2005/0176624 A1 | 8/2005 | Thompson et al. | |
| 2005/0186447 A1 | 8/2005 | Grushin et al. | |
| 2005/0196775 A1 | 9/2005 | Swager et al. | |
| 2005/0220714 A1 | 10/2005 | Kauzlarich et al. | |
| 2005/0226775 A1 | 10/2005 | Aker et al. | |
| 2005/0263758 A1 | 12/2005 | Treacher et al. | |

(56) References Cited

U.S. PATENT DOCUMENTS

| | | | |
|---|---|---|---|
| 2005/0285517 | A1 | 12/2005 | Yu et al. |
| 2006/0024707 | A1 | 2/2006 | Deans et al. |
| 2006/0029829 | A1 | 2/2006 | Thompson et al. |
| 2006/0057425 | A1 | 3/2006 | Grushin et al. |
| 2006/0058524 | A1 | 3/2006 | Falcou et al. |
| 2006/0073607 | A1 | 4/2006 | Rose et al. |
| 2006/0120917 | A1 | 6/2006 | Swager et al. |
| 2006/0135772 | A1 | 6/2006 | Huo |
| 2006/0173145 | A1 | 8/2006 | Pawlow et al. |
| 2006/0270846 | A1 | 11/2006 | Karpishin et al. |
| 2007/0081921 | A1 | 4/2007 | Swager et al. |
| 2007/0083066 | A1 | 4/2007 | Bohm et al. |
| 2008/0085566 | A1 | 4/2008 | Swager et al. |
| 2009/0215189 | A1 | 8/2009 | Swager et al. |
| 2010/0063225 | A1 | 3/2010 | Swager et al. |
| 2010/0112715 | A1 | 5/2010 | Swager et al. |
| 2010/0168352 | A1 | 7/2010 | Arriola et al. |
| 2010/0213451 | A1 | 8/2010 | Swager et al. |
| 2010/0310424 | A1 | 12/2010 | Rose et al. |
| 2011/0142717 | A1 | 6/2011 | Swager et al. |
| 2011/0175035 | A1 | 7/2011 | Swager et al. |

FOREIGN PATENT DOCUMENTS

| | | |
|---|---|---|
| DE | 19806037 | 8/1999 |
| EP | 0 259 951 A2 | 3/1988 |
| EP | 0581058 | 2/1994 |
| EP | 0 748 805 A1 | 12/1996 |
| EP | 1 011 154 A1 | 6/2000 |
| JP | 06-322078 A | 11/1994 |
| WO | WO-89/00593 A1 | 1/1989 |
| WO | WO-95/16681 A1 | 6/1995 |
| WO | WO-98/05693 A1 | 2/1998 |
| WO | WO 99/19419 | 4/1999 |
| WO | WO-99/57222 A1 | 11/1999 |
| WO | WO-00/05774 A1 | 2/2000 |
| WO | WO 00/53655 | 9/2000 |
| WO | WO-01/57140 A1 | 8/2001 |
| WO | WO-02/16463 A2 | 2/2002 |
| WO | WO 02/074997 A1 | 9/2002 |
| WO | WO 02/079268 A2 | 10/2002 |
| WO | WO-03/048226 A2 | 6/2003 |
| WO | WO-2004/057014 A2 | 7/2004 |
| WO | WO-2005/030681 A1 | 4/2005 |
| WO | WO 2005/086617 A2 | 9/2005 |
| WO | WO-2006/081345 A1 | 8/2006 |
| WO | WO-2006/085319 A2 | 8/2006 |
| WO | WO-2008/019086 A2 | 2/2008 |
| WO | WO-2008/039529 A1 | 4/2008 |
| WO | WO-2008/042289 A2 | 4/2008 |
| WO | WO-2008/136805 A2 | 11/2008 |

OTHER PUBLICATIONS

Dai et al. Sensors and sensor arrays based on conjugated polymers and carbon nanotubes. Pure Appl. Chem. 2002, vol. 74, No. 9, pp. 1753-1772.*

Disney, M.D. et al., "*Visual Detection of Bacteria with Carbohydrate-Containing Fluorescent Polymers*," J. Am. Chem. Soc. 2004, 126, 13343-13346.

Zheng, J., et al., "*Energy Transfer from Biotinylated Poly(p-phenylene ethynylene): New Insights for Amplified Fluorescence-Based Biosensors*," Chem. Commun., 2004, 2798-2799 vol. 24.

Zheng, J. et al., Supporting Information for "*Energy Transfer from Biotinylated Poly)p-phenylene ethynylene): New Insights for Amplified Fluorescence-Based Biosensors*", Chem. Comm., Dec. 2004, vol. 24, pp. 2798-2799.

Liu, et al., "Effect of Chromophore-Charge Distance on the Energy Transfer Properties of Water-Soluble Conjugated Oligomers," *J. Am. Chem. Soc.*, vol. 125, pp. 6705-6714 (2003).

McQuade, et al., "Conjugated Polymer-Based Chemical Sensors," *Chem. Rev.*, vol. 100, pp. 2537-2574 (2000).

Wang, et al., "Fluorescein Provides a Resonance Gate for FRET from Conjugated Polymers to DNA Intercalated Dyes," *J. Am. Chem. Soc.*, vol. 126, pp. 5446-5451 (2004).

International Search Report dated Feb. 23, 2006, PCT/US2005/033261.

Hoffmeister et al. "Triptycene Polymers," J. Polymer Science 1969, 7, 55-72.

EP 02024311.9, Jan. 3, 2003, European Search Report.

PCT/US2005/033261, Feb. 23, 2006, International Search Report and Written Opinion.

PCT/US2005/033261, Mar. 29, 2007, International Preliminary Report on Patentability.

PCT/US2006/045390, Jun. 12, 2007, Invitation to Pay Additional Fees.

PCT/US2006/045390, Sep. 24, 2007, International Search Report and Written Opinion.

PCT/US2006/045390, Jun. 5, 2008, International Preliminary Report on Patentability.

PCT/US2007/017380, Jan. 4, 2008, Invitation to Pay Additional Fees.

PCT/US2007/017380, Apr. 8, 2008, International Search Report and Written Opinion.

PCT/US2007/017380, Nov. 10, 2008, International Preliminary Report on Patentability.

PCT/US2007/020961, Dec. 14, 2007, International Search Report and Written Opinion.

PCT/US2007/020961, Apr. 9, 2009, International Preliminary Report on Patentability.

PCT/US2007/020992, Feb. 8, 2008, Invitation to Pay Additional Fees.

PCT/US2007/020992, Apr. 4, 2008, International Search Report and Written Opinion.

PCT/US2007/020992, Apr. 9, 2009, International Preliminary Report on Patentability.

PCT/US2007/022670, Oct. 27, 2008, International Search Report and Written Opinion.

PCT/US2007/022670, May 7, 2009, International Preliminary Report on Patentability.

PCT/US2007/021370, Feb. 22, 2008, Invitation to Pay Additional Fees.

PCT/US2007/021370, Jun. 13, 2008, International Search Report and Written Opinion.

PCT/US2007/021370, Apr. 16, 2009, International Preliminary Report on Patentability.

[No Author Listed] Chemical Structure for Biphenylene. CAS No. 259-79-0. Downloaded Dec. 12, 2005.

[No Author Listed] Institute for Soldier Nanotechnologies. Downloaded from http://web.mit.edu/isn/industryday/index.html on Jan. 30, 2003.

Abraham et al., "Hydrogen bonding. Part 29. Characterization of 14 Sorbent Coatings for Chemical Microsensors using a New Solvation Equation," J. Chem. Soc. Perkin Trans. 1995, 2, 369-378.

Achyuthan, KE, et al., "Fluorescence superquenching of conjugated polyelectrolytes: applications for biosensing and drug discovery", Journal of Materials Chemistry, vol. 15 (27-28): 2648-2656, 2005.

Albert et al., Designing optical sensor arrays with enhanced sensitivity for explosives detection. Proceeedings of the SPIE—The International Society for Optical Engineering. Orlando, Florida. Apr. 13-17, 1998;3392(1-2):426-31. Abstract Only.

Amara et al., "Synthesis and Properties of Poly(phenylene ethynylene)s with Pendant Hexafluoro-2-propanol Groups," Macromolecules 2005, 38, 9091-9094.

Amara, J. et al., "Incorporation of Internal Free Volume: Synthesis and Characterization of Iptycene-Elaborated Poly(butadiene)s," Macromolecules 2004, 37, 3068-3070.

Arias-Marin et al., Amphiphilic Phenyl-Ethynylene Polymers and Copolymers. Synthesis, Characterization, and Optical Emission Properties. Macromolecules. 2003;36:3570-79.

Armengaud et al., "Electrochemistry of conducting polypyrrole films containing cobalt porphyrin," J. Electroanal. Chem., 1990, 277:197-211.

(56) References Cited

OTHER PUBLICATIONS

Audebert et al., "Description of New Redox and Conducting Polymers Based on Copper Containing Units; Emphasis on the Role of Copper in the Electron Transfer Mechanism," Synthetic Metals, 1991, 3049-3052.
Audebert et al., "Redox and Conducting Polymers Based on Salen-Type Metal Units; Electrochemical Study and Some Characteristics," New Journal of Chemistry, 1992 16(6):697-703.
Audebert et al., "Synthesis and Characteristics of New Redox Polymers Based on Copper Containing Units; Evidence for the Participation of Copper in the Electron Transfer Mechanism," New Journal of Chemistry, 1991, 15(4):235-237.
Baldo et al., "Excitonic singlet-triplet ratio in a seminconducting organic thin film," Phys. Rev. B., 1999, 60(20), 14422-14428.
Baldo et al., "High-efficiency fluorescent organic light-emitting devices using a phosphorescent sensitizer," Nature, 2000, 403, 750-753.
Barigelletti et al., "Temperature Dependence of the Luminescence of Cyclometalated Palladium(II), Rhodium(III), Platinum(II), and Platinum(IV) Complexes," Inorg. Chem. 1988, 27, 3644-47.
Bedioui et al., "Electrochemistry of conducting polypyrrole films containing cobalt porphyrin, Part 2. New Developments and inclusion of metallic aggregates in the coordination polymer," J. Electroanal. Chem., 1991, 297:257-269.
Bedioui et al., "Electrooxidative polymerization of cobalt, nickel and manganese salen complexes in acetonitrile solution," J. Electroanal. Chem., 1991, 301:267-274.
Bedioui et al., "Poly(Pyrrole-Manganese Tetraphenylporphyrin) film Electrodes in Acetonitrile Solution," J. Electroanal. Chem., 1988, 239:433-439.
Bergstedt, T, et al., "Superquenching of fluorescent polyelectrolytes and its applications for chemical and biological sensing," in Organic Photonic Materials and Devices III, Bernard Kippelen, Donal D. C. Bradley, Editors, Proceedings of SPIE vol. 4279, 94-100 (2001).
Bettelheim et al., "Electrochemical Polymerization of Amino-, Pyrrole-, and Hydroxy-Substituted Tetraphenylporphyrins," Inorganic Chemistry, 1987, 26(7):1009-1017.
Bowyer et al., Electrochemical reduction of vicinal dinitro compounds. J Org Chem. 1988;53(22):5234-5239.
Brabec, Christoph, et al. "Plastic Solar Cells", Adv. Funct. Mater, 2001, vol. 11, No. 1, pp. 15-26.
Bredas et al., "Electronic Structure of Poly(paraphenylene vinylene): Influence of Copolymerization and Derivatization on Light-Emitting Characteristics," Am. Chem. Scoc., Div. Polym. Chem., 1994, 35, 185-186.
Brooks et al., "Synthesis and Characterization of Phosophorescent Cyclometalated Platinum Complexes," Inorg. Chem., 2002, 41(12), 3055-3066.
Brown et al., "Core-referenced ratiometric fluorescent potassium ion sensors using self-assembled ultrathin films on europium nanoparticles," IEEE Sensors Journal, 2005, 5(6), 1197-1205.
Brown et al., Fluorescence-enhancement sensing of ammonia and hydrazines via disruption of the internal hydrogen bond in a carbazolopyridinophane. Sensors Actuators B. 2005;110:8-12.
Bustin, Absolute quantification of mRNA using real-time reverse transcription polymerase chain reaction assays. J Mol Endocrinol. Oct. 2000;25(2):169-93.
Cabarcos et al., "Effect of the Molecular Weight and the Ionic Strength on the Photoluminescence Quenching of Water-Soluble Conjugated Polymer Sodium Poly[2-(3-thienyl)ethyloxy-4-butylsulfonate]," Macromolecules, 2005, 38(25), 10537-10541.
Cameron et al., "A conjugated polymer/redox polymer hybrid with electronic communication between metal centres," Chem. Commun., 1997, 303-304.
Carrabba et al., Hydrogen bonding in the lowest singlet n-pi-star excited state of pyrimidine. J Phys Chem. 1985;89:674-77.
Chassot et al., "cis-Bis(2-phenylpyridine platinum(II)(CBPPP): A Simple Molecular Platinum Compound," Inorg. Chem., 1984, 23(25), 4249-4253.

Chassot et al., "Cyclometalated Complexes of Platinum(II): Homoleptic Compounds with Aromatic C,N Ligands," Inorg. Chem., 1987, 26(17), 2814-2818.
Chassot et al., "Photochemical Preparation of Luminsecent Platinum(IV) Complexes via Oxidative Addition on Luminescent Platinum(II) Complexes," J. Am. Chem. Soc., 1986, 108, 6084-6085.
Chatterjee et al.,Synthesis of Functionalized Olefins by Cross and Ring-Closing Metatheses. J Am Chem Soc. 2000;122(15):3783-84.
Chen, L., et al., "Surfactant-Induced Modification of Quenching of Conjugated Polymer Fluorescence by Electron Acceptors: Applications for Chemical Sensing," Chem. Phys. Lett. 330 (1-2) (2000) pp. 27-33.
Chen, Liaohai et al., "Tuning the properties of conjugated polyelectrolytes through surfactant complexation," J. Am. Chem. Soc., 2000, vol. 122 No. 38, pp. 9302-9303.
Chen, Liaohai, et al., "Highly sensitive biological and chemical sensors based on reversible fluoresence quenching in a conjugated polymer," PNAS, Oct. 26, 1999, vol. 96 No. 22, 12287-12292.
Choi et al, Oxygen-sensitive reverse-phase optode membrane using silica gel-absorbed ruthenium(II) complex embedded in gelatin film. Anal. Chim. Acta 1999, 387, 197-205.
Costa-Fernandez et al., "Sol-gel immobilized room-temperature phosphorescent metal-chelate as luminescent oxygen sensing material," *Anal. Chim. Acta.*, 1998, 360, 17-26.
Cotts, Patricia M., et al., "Equilibrium Flexibility of a Rigid Linear Conjugated Polymer," Macromolecules, 1996, vol. 29, pp. 7323-7328.
Cumming et al., "Using Novel Fluorescent Polymers as Sensory Materials for Above-Ground Sensing of Chemical Signature Compounds Emanating from Buried Landmines," IEEE Transactions on Geoscience and Remote Sensing, 2001, 39:1119-1128.
Dagani, Ron, "A Better Sensor for Nerve Gas," C&EN, Mar. 10, 2003, p. 12.
Dahm et al., "Catalytic Reduction of Iodoethane and 2-Iodopropane at Carbon Electrodes Coated with Anodically Polymerized Films of Nickel(II) Salen," Analytical Chemistry, 1994, 66(19):3117-3123.
Davey et al., New Rigid Backbone Conjugated Organic Polymers with Large Fluorescence Quantum Yields. J Chem Soc Chem Commun. 1995;1433-34.
Deans, Robert, et al., "A Poly(p-phenyleneethynylene) with a Highly Emissive Aggregated Phase", J. Am. Chem. Soc., 2000, vol. 122, pp. 8565-8566.
Decher, "Fuzzy Nanoassemblies: Toward Layered Polymeric Multicomposites," Science, 1997, 277(5330), 1232-1237.
Demchenko et al., "The problem of self-calibration of fluorescence signal in microscale sensor systems," Lab on a Chip, 2005, 5, 1210-1223.
Deng et al., "Direct Observation of the "Pac-Man" Effect from Dibenzofuran-Bridged Cofacial Bisporphyrins," J. Am. Chem. Soc. 2000, 122, 410-411.
Dijkstra et al., "Shape-Persistent Nanosize Organometallic Complexes: Synthesis and Application in a Nanofiltration Membrane Reactor," J. Org. Chem., 2003, vol. 68, No. 3, pp. 675-685.
Disney, M.D. et al., "Detection of Bacteria with Carbohydrate-Functionalized Fluorescent Polymers," J. Am. Chem. Soc. 2004, 126, 13343-13346.
Dougherty et al., "Photodynamic Therapy," J. Natl. Cancer Inst., 1998, 90(12), 889-905.
Dudek et al., Synthesis and energy-transfer properties of hydrogen-bonded oligofluorenes. J Am Chem Soc. Aug. 24, 2005;127(33):11763-8.
Dwight et al., "Perturbation of Fluorescence by Nonspecific Interactions between Anionic Poly(phenylenevinylene)s and Proteins: Implications for Biosensors," J. Am. Chem. Soc., 2004, 126(51), 16850-16859.
Ellis et al., Conductive Polymer Films as Ultrasensitive Chemical Sensors for Hydrazine and Monomethylhydrazine Vapor. Anal Chem. 1996;68:817-22.
European Search Report for EP 02024311.9 mailed Jan. 3, 2003.
Ewing et al., Detection of volatile vapors emitted from explosives with a handheld ion mobility spectrometer. Field Anal Chem Technol. 2001;5:215-21.

(56) References Cited

OTHER PUBLICATIONS

Famulok et al., Nucleic acid aptamers-from selection in vitro to applications in vivo. Acc Chem Res. Sep. 2000;33(9):591-9.
Fan, C, et al., "High-Efficiency Fluorescence Quenching of Conjugated Polymers by Proteins," J. Am. Chem Soc., 2002, 124(20): pp. 5642-5643.
Fan, C, et al., "Photoluminescence Quenchers of Water Soluble Conjugated Polymers by Viologen Derivatives: Effect of Hydrophobicity," Langmuir, 2003, 19(8): pp. 3554-3556.
Fan, C, S., et al, "Beyond superquenching: Hyper-efficient energy transfer from conjugated polymers to gold nanoparticles," PNAS, 2003, 100(11): pp. 6297-6301.
Fiesel, Rainer, et al., "A chiral poly(para-phenyleneethynylene) (PPE) derivative," Macromol. Rapid Commun., 1998, vol. 19, No. 8, pp. 427-431.
Fiesel, Rainer, et al., "Aggregation-induced CD effects in chiral poly(2,5-dialkoxy-1,4-phenylene)s," Acta Polym., 1998, vol. 49, pp. 445-449.
Fiesel, Rainer, et al., "On the Solid State Aggregation of Chiral Substituted Poly(para-phenylene)s (PPPs)," Synthetic Metals, 1999, vol. 102, pp. 1457-1458.
Fu, Dian-Kui, et al., "Alternating Poly(PyridylVinylenePhenyleneVinylene)s: Synthesis and Solid State Organizations," Tetrahedron, 1997, vol. 53, No. 45, pp. 15487-15494.
Funhoff et al., Cationic polymethacrylates with covalently linked membrane destabilizing peptides as gene delivery vectors. J Control Release. Jan. 3, 2005;101(1-3):233-46.
Garner, C., et al., "Challenges for dielectric materials in future integrated circuit technologies," Microelectronics Reliability 2005, 45, 919-924.
Gaylord, B.S, et al., "DNA Hybridization Detection with Water-Soluble Conjugated Polymers and Chromophore-Labeled Single Stranded DNA," J. Am. Chem Soc., 2003, 125(4): pp. 896-900.
Gaylord, B.S., et al., "SNP detection using peptide nucleic acid probes and conjugated polymers: Applications in neurodegenerative disease identification," PNAS, vol. 102, No. 1, pp. 34-39 (2005).
Gaylord, B.S., et al., "Water-Soluble Conjugated Oligomers: Effect of Chain Length and Aggregation on Photoluminescence-Quenching Efficiencies," J. Am. Chem. Soc. 2001, 123(26): 6417-6418.
Gaylord, Brent S., et al., "DNA detection using water-soluble conjugated polymers and peptide nucleic acid probes," PNAS, Aug. 20, 2002, vol. 99, No. 17, pp. 10954-10957.
Gianini et al., "Chiral Cyclometalated Platinum(II) Complexes with Derivatives of Thienylpyridine as Ligands: Helical Distortion of the Square Planar (SP-4) Geometry," Inorg. Chem, 1997, 36(26), 6094-6098.
Gianini et al., "Square Planar (SP-4) and Octahedral (OC-6) Complexes of Platinum (II) and - (IV) with Predetermined chirality at the Metal Center," Inorg. Chem., 1996, 35(17), 4889-4895.
Goldfinger et al., "Fused polycyclic aromatics via electrophile-induced cyclization reactions: application to the synthesis of graphite ribbons", J. Am. Chem. Soc., 1994, vol. 116, pp. 7895-7896.
Goldsby et al., "Oxidation of Nickel(II) Bis(salicylaldimine) Complexes: Solvent Control of the Ultimate Redox Site," Polyhedron, 1989, 8(1):113-115.
Goldsby et al., "Symmetric and Unsymmetric Nickel(II) Schiff Base Complexes; Metal-Localized Localized Versus Ligand-Localized Oxidation," J. Coord. Chem., 1988, 19:83-90.
Grate et al., "Hydrogen Bond Acidic Polymers for Surface Acoustic Wave Vapor Sensors and Arrays," Anal. Chem. 1999, 71, 1033-1040.
Grate, "Acoustic Wave Microsensor Arrays for Vapor Sensing," Chem Rev. 2000, 100, 2627-2647.
Guice et al., "Nanoscale internally referenced oxygen sensors produced from self-assembled nanofilms on fluorescent nanoparticles," Journal of Biomedical Optics, 2005, 10(6), 064031-1-064031-10.
Guimaraes et al., On the fluoresence of pyrrole derivative oligomer. Mater Sci Engineer C. 2008;28:1076-81.
Halkyard, Carrie E., et al., "Evidence of Aggregate Formation for 2,5-Dialkylpoly (p-phenyleneethynylenes) in Solution and Thin Films," Macromolecules, Nov. 25, 1998, vol. 31, No. 25, pp. 8655-8659.
Hard et al., Fluorescence studies of a single tyrosine in a type II DNA binding protein. Biochemistry. Jan. 10, 1989;28(1):396-406.
Harrison, Benjamin S., et al., "Amplified Fluorescence Quenching in a Poly(p-phenylene)-Based Cationic Polyelectrolyte," J. Am. Chem. Soc., Aug. 16, 2001, vol. 122, No. 35, pp. 8561-8562.
Havemann, R., "High-Performance Interconnects: An Integration Overview," Proceedings of the IEEE 2001, 89(5), 586-601.
Heeger, P., et al., "Making sense of polymer-based biosensors," PNAS, vol. 96, No. 22, pp. 12219-12221 (1999).
Herbich et al. "Fluorescence Quenching by Pyridine and Derivatives Induced by Intermolecular Hydrogen Bonding to Pyrrole-Containing Heteroaromatics," J. Phys. Chem. A. 2002, 106, 2158-2163.
Hill et al., "A Mechanistic Study of the Photochemically Initiated Oxidative Addition of Isopropyl Iodide to Dimethl(1,10-phenanthroline)platinum(II),"J. Am. Chem. Soc., 1985, 107(5), 1218-1225.
Hoferkamp et al., "Surface-Modified Electrodes Based on Nickel(II) and Copper(II) Bis(salicylaldimine) Complexes," Chemistry of Materials, 1989, 1(3):348-352.
Horwitz et al., "Oxidative Electropolymerization of Metal Schiff-Base Complexes," Mol. Cryst. Liq. Cryst., 1988, 160:389-404.
Houk et al., "[C-H•••O] Interactions as a Control Element in Supramolecular Complexes: Experimental and Theoretical Evaluation of Receptor Affinities for the Binding of Bipyridinium-Based Guests by Catenated Hosts," J. Am. Chem. Soc., 1999, 121(7), 1479-1487.
Houser et al.. Rational materials design of sorbent coatings for explosives: applications with chemical sensors. Talanta. May 10, 2001;54(3):469-85.
Huang et al., "Design of a Modular-Based Fluorescent Conjugated Polymer for Selective Sensing," Angew. Chem. Int. Ed., 2004, 43(42), 5635-5638.
Huang et al., Nanostructured polyaniline sensors. Chem Euro J. Mar. 19, 2004;10(6)1314-9.
Höger, Sigurd, et al., "Synthesis, Aggregation, and Adsorption Phenomena of Shape-Persistent Macrocycles with Extraannular Polyalkuly Substituents," J. Am. Chem. Soc., May 22, 2001, vol. 123, No. 24, pp. 5651-5659.
International Search Report and Written Opinion mailed Feb. 23, 2006, PCT/US2005/033261.
International Preliminary Report on Patentability for PCT/US2005/033261 mailed Mar. 29, 2007.
Invitation to Pay Additional Fees for PCT/US2006/045390 mailed Jun. 12, 2007.
International Search Report and Written Opinion for PCT/US2006/045390 mailed Sep. 24, 2007.
International Preliminary Report on Patentability for PCT/US2006/045390 mailed Jun. 5, 2008.
Invitation to Pay Additional Fee for PCT/US2007/017380 mailed Jan. 4, 2008.
International Search Report and Written Opinion mailed Apr. 8, 2008 in PCT/US2007/017380.
International Preliminary Report on Patentability mailed Nov. 10, 2008 in PCT/US2007/017380.
International Search Report and Written Opinion mailed Dec. 14, 2007 in PCT/US2007/020961.
International Preliminary Report on Patentability dated Mar. 31, 2009, mailed Apr. 9, 2009, in PCT/US2007/020961.
Invitation to Pay Additional Fee for PCT/US2007/020992 mailed Feb. 8, 2008.
International Search Report and Written Opinion for PCT/US2007/020992 mailed Apr. 4, 2008.
International Preliminary Report on Patentability for PCT/US2007/020992 mailed Apr. 9, 2009.
International Search Report and Written Opinion mailed Oct. 27, 2008 in PCT/US2007/022670.
International Preliminary Report on Patentability dated Apr. 28, 2009, mailed May 7, 2009, in PCT/US2007/022670.

(56) References Cited

OTHER PUBLICATIONS

Invitation to Pay Additional Fee for PCT/US2007/021370 mailed Feb. 22, 2008.
International Search Report and Written Opinion mailed Jun. 13, 2008 in PCT/US2007/021370.
International Preliminary Report on Patentability for PCT/US2007/021370 mailed Apr. 16, 2009 (M0925.70182W000).
Jayarajah et al., "Oxygen Diffusion and Permeability in Alkylaminothionylphosphazene Films Intended for Phosphorescence Barometry Applications," Macromolecules, 2000, 33(15), 5693-5701.
Jensen et al., Cytoplasmic delivery and nuclear targeting of synthetic macromolecules. J Control Release. Feb. 21, 2003;87(1-3):89-105.
Jolliet et al., "Cyclometalated Complexes of Palladium(II) and Platinum(II): cis-Configured Homoleptic and Heteroleptic Compounds with Aromatic CN Ligands," Inorg. Chem., 1996, 35(17), 4883-4888.
Joly et al., "Highly Effective Water-Soluble Fluorescence Quenchers of Conjugated Polymer Thin Films in Aqueous Environments," Macromolecules, 2006, 39(21), 7175-7177.
Jones, R.M., et al., "Building highly sensitive dye assemblies for biosensing from molecular building blocks," PNAS USA 2001, 98(26): 14769-14772.
Jones, R.M., et al., "Superquenching and Its Applications in J-Aggregated Cyanine Polymers," Langmuir,:2001, 17, 2568-2571.
Jones, R.M., et al., "Tuning of Superquenching in Layered and Mixed Fluorescent Polyelectrolytes," J. Am. Chem. Soc. 2001, 123: 6726-6727.
Katayama et al., Vinylideneruthenium complexes in catalysis. Coord Chem Revs. 2004;248:1703-15.
Kim et al. "Nonspecific Interactions of a Carboxylate-Substituted PPE with Proteins. A Cautionary Tale for Biosensor Applications," Langmuir, 2005, 21(17), 7985-7989.
Kim et al., "Control of conformational and interpolymer effects in conjugated polymers," Nature, 2001, 411, 1030-1034.
Kim et al., "Directing Energy Transfer within Conjugated Polymer Thin Films," J. Am. Chem. Soc., 2001, 123(46), 11488-11489.
Kim et al., "Ion-Specific Aggregation in Conjugated Polymers: Highly Sensitive and Selective Fluorescent Ion Chemosensors," Agnew Chem. Int. Ed., 2000, 39(21), 3868-3872.
Kim et al., "Nanoscale Fibrils and Grids: Aggregated Structures from Rigid-Rod Conjugated Polymers," Macromolecules, 1999, 32 (5), 1500-1507.
Kim et al., "Structural Control in Thin Layers of Poly)P-phenyleneethynylene)s: Photophysical Studies of Langmuir and Langmuir-Blodgett Films," J. Am. Chem. Soc., 2002, 124(26), 7710-7718.
Kim et al., "Ultrafast Energy-Transfer Dynamics between Block Copolymer and π-Conjugated Polymer Chains in Blended Polymeric Systems," Chemistry of Materials, 13(8), 2666-2674, 2001.
Kim, T.-H. et al. "A Fluorescent Self-Amplifying Wavelength Responsive Sensory Polymer for Fluoride Ion," Angew. Chem. Int. Ed. 2003, 42, 4803-4806.
Kraft, Arno, et al., "Electroluminescent Conjugated Polymers—Seeing Polymers in a New Light," Agnew. Chem. Int. Ed. 1998, 37, 402-428.
Kui et al., "Structures, Photoluminescence, and Reversible Vapoluminescence Properties of Neutral Platinum(II) Complexes Containing Extended p-Conjugated Cyclometalated Ligands," J. Am. Chem. Soc. 2006, 128, 8297-309.
Kumaraswamy, S., et al., "Fluorescent-conjugated polymer superquenching facilitates highly sensitive detection of proteases," PNAS, May 18, 2004, 101(20): pp. 7511-7515.
Kushon, S.A., et al., "Detection of DNA Hybridization via Fluorescent Polymer Superquenching," Langmuir, 2002, 18(20): pp. 7245-7249.
Kushon, S.A., et al., "Detection of single nucleotide mismatches via fluorescent polymer superquenching," Langmuir, 2003, 19(20): pp. 6456-6464.

Köhler, Bernhard, et al., "Novel Chiral Macrocycles Containing Two Electronically Interacting Arylene Chromophores," Chem. Eur. J., 2001, vol. 7, No. 14, pp. 3000-3004.
Lamansky et al., "Highly Phosphorescent Bis-Cyclometalated Iridium Complexes: Synthesis, Photophysical Characterization, and Use in Organic Light Emitting Diodes," J. Am. Chem. Soc., 2001, 123(18), 4304-4312.
Lamba et al., "Imine-Bridged Planar Poly(p-phenylene) Derivatives for Maximization of Extended π-Conjugation. The Common Intermediate Approach," J. Am. Chem. Soc., 1994, 116(26), 11723-11736.
Langeveld-Voss et al., "Circular Dichroism and Circular Polarization of Photoluminescence of Highly Ordered Poly{3,4-di[(S)-2-methylbutoxy]thiophene}," J. Am. Chem. Soc., 1996, vol. 118, No. 20, pp. 4908-4909.
Levitsky, et al., "Rational Design of a Nile Red/Polymer Composite Film for Fluorescence Sensing of Organophosphonate Vapors Using Hydrogen Bond Acidic Polymers," Anal. Chem. 2001, 73, 3441-3448.
Levitsky, et al., "Signal Amplification in Multichromophore Luminescence-Based Sensors," J. Phys. Chem. B, 2001, 105, 8468-8473.
Levitsky, Igor A., et al., "Energy Migration in a Poly(phenylene ethynylene): Determination of Interpolymer Transport in Anisotropic Langmuir-Blodgett Films," J. Am. Chem. Soc., 1999, vol. 121, No. 7, pp. 1466-1472.
Levitsky, Igor A., et al., "Mass and Energy Transport in Conjugated Polymer Langmuir-Blodgett Films; Conductivity, Fluorescence, and UV-Vis Studies," Macromolecules, Mar. 27, 2001, vol. 34, No. 7, pp. 2315-2319.
Li et al., Water-Soluble Poly(acrylic acid) Grafted Luminescent Silicon Nanoparticles and Their Use as Fluorescent Biological Staining Labels. Nano Letters. 2004; 4(8):1463-1467.
Li, Mei, et al., "Novel Surfactant-Free Stable Colloidal Nanoparticles Made of Randomly Carboxylated Polystyrene Ionomers," Macromolecules, 1997, vol. 30, No. 7, pp. 2201-2203.
Liao et al., "Quantification of Amplified Quenching for Conjugated Polymer Microsphere Systems," Langmuir, 2007, 23(1), 112-115.
Lim et al., Transferrin-oligomers as potential carriers in anticancer drug delivery. Pharm Res. Nov. 2004; 21(11):1985-92.
Lipkowitz et al., A protocol for determining enantioselective binding of chiral analytes on chiral chromatographic surfaces. J Am Chem Soc. 1988;110:3446-52.
Liu et al., "Fluorescence Quenching Mechanism of a Polyphenylene Polyelectrolyte with Other Macromolecules: Cytochrome c and Dendrimers," Langmuir, 2005, 21(5), 1687-1690.
Liu, B., et al., "Homogeneous Fluorescence-Based DNA Detection with Water-Soluble Conjugated Polymers," Chem. Matter, vol. 16, pp. 4467-4476 (2004).
Liu, B., et al., "Methods for strand-specific DNA detection with cationic conjugated polymers suitable for incorporation into DNA chips and microarrays," PNAS, vol. 102, No. 3, pp. 589-593 (2005).
Liu, B., et al., "Optimization of the Molecular Orbital Energies of Conjugated Polymers for Optical Amplification of Fluorescent Sensors," J. Am. Chem. Soc., vol. 138, pp. 1188-1196 (2006).
Long, T. et al., "Molecular Design of Free Volume as a Route to Lowк Dielectric Materials," J. Am. Chem. Soc. 2003, 125, 14113-14119.
Lu L., et al., "Biocidal activity of a light-absorbing fluorescent conjugated polyelectrolyte", Langmuir, 2005, vol. 21, No. 22, pp. 10154-10159.
Lu, L., et al., "Cyanine pendant polymers on nanoparticles and in solution: superquenching and sensing applications," Polymeric Materials Science and Engineering, 2002, 86: pp. 17-18.
Lu, L., et al., "Self-assembled 'polymers' on nanoparticles: superquenching and sensing applications," Polymer Preprints (American Chemical Society, Division of Polymer Chemistry), 2002, 43: pp. 124-125.
Lu, L., et al., "Superquenching in cyanine pendant poly-L-lysine dyes: dependence on molecular weight, solvent and aggregation," Journal of the American Chemical Society, 2002, 124: pp. 483-488.
Lu, L., et al., "Surface-Enhanced Superquenching of Cyanine Dyes as J-Aggregates on Laponite Clay Nanoparticles," Langmuir, 2002, 18(20): pp. 7706-7713.

(56) References Cited

OTHER PUBLICATIONS

Luo, Laibin, et al., "Thermodynamic Stabilization Mechanism of Block Copolymer Vesicles," J. Am. Chem. Soc., 2001, vol. 123, No. 5, pp. 1012-1013.
MacDiarmid, Polyanaline and polypyrrole: Where are we headed? Synthetic Metals. 1997;84:27-34.
Maestri et al., "Absorption Spectra and Luminescence Properties of Isomeric Platinum(II) and Palladium(II) Complexes Containing 1,1'-Biphenyldiyl, 2-Phenylpyridine, and 2, 2'-Bipyridine as Ligands," Helvetica Chimica Acta 1988, 71, 1053-59.
Maex, K. et al., "Low dielectric constant materials for microelectronics," Journal of Applied Physics 2003, 93(11), 8793-841.
Maier, G., "Low dielectric constant polymers for microelectronics," Prog. Polym. Sci. 2001, 26, 3-65.
Martin, et al., "Picosecond Laser Photolysis Studies of Deactivation Processes of Excited Hydrogen-Bonding Complexes. 2. Dibenxocarbazole-Pyridine Systems," J. Phys. Chem. 1982, 86, 4148-4156.
Martin, S. et al., "Development of a Low-Dielectric-Constant Polymer for the Fabrication of Integrated Circuit Interconnect," Adv. Mater. 2000, 12(23), 1769-78.
Matloka et al., The acyclic diene metatheis (ADMET) polymerization approach to silicon containing materials. J Mol Catalysis. 2006;257:89-98.
Manes et al., Extraction-spectrophotometric determination of hydrazine with 2-hydroxy-1-naphthaldehyde. Analyst. 1987;112:1183-84.
McGill, et al., "Choosing polymer coatings for chemical sensors," Chemtech 1994, 24, 27-37.
McQuade, D. tyler, et al., "Two-Dimensional Conjugated Polymer Assemblies: Interchain Spacing for Control of Photophysics," J. Am. Chem. Soc., 2000, vol. 122, No. 24, pp. 5885-5886.
Medintz et al., "Quantum dot bioconjugates for imaging, labelling and sensing," Nature Materials, 2005, 4(6), 435-446.
Miao, Yi-Jun, et al., "Fluorescence Sensory Polymers Containing Rigid Non-planar Aromatic Scaffolds," Proceedings of the 1997 Boston meeting, vol. 39, No. 2, pp. 1081-1082, Aug. 23-27, 1998, Polym. Prepr. Div. Polym. Chem. Am .Chem .Soc.; Polymer Preprints, Division of Polymer Chemistry, American Chemical Society, Aug. 1998 ACS, Washington D.C.
Mitschke, Ullrich et al., "The electroluminescence of organic materials," J. Mater. Chem., 2000, vol. 10, pp. 1471-1507.
Miyasaka, et al., "Femtosecond-Picosecond Laser Photolysis Studies on the Mechanisms of Fluorescence Quenching Induced by Hydrogen-Bonding Interactions—1-Pyrenol-Pyridine Systems," J. Phys. Chem. 1993, 97, 8222-8228.
Moisy et al., "Epoxidation of cis-cyclooctene by Molecular Oxygen Electrocatalysed by Polypyrrole-Manganese Porphyrin Film Modified Electrodes," J. Electroanal. Chem., 1988, 250:191-199.
Moon et al., Live-cell-permeable poly(p-phenylene ethynylene). Angew Chem Int Ed Engl. 2007;46(43):8223-5.
Moon, Joong Ho, et al., "Capture and detection of a quencher labeled oligonucleotide by poly)phenylene ethynylene) particles," Chem. Commun., Jan. 2003, vol. 1, pp. 104-105.
Morgen, M., et al., "Low Dielectric Constant Materials for ULSI Interconnects," Annu. Rev. Mater. Sci. 2000, 30, 645-80.
Morin et al., "Syntheses of Conjugated Polymers Derived from N-Alkyl-2,7-carbazoles," Macromolecules, 2001, 34(14), 4680-4682.
Moroni et al., Rigid Rod Conjugated Polymers for Nonlinear Optics. 3. Intramolecular H Bond Effects on Poly(phenyleneethynylene) Chains. Macromolecules. 1997;30:1964-72.
Murarka, S., "Materials aspects of copper interconnection technology for semiconductor applications," Materials Science and Technology 2001, 17, 749-58.
Ng et al., Syntheses and characterisation of electrically conductive and fluorescent poly[3-(ω-bromoalkyl)thiophenes]. Synthetic Metals. 1999;100:269-77.
Nie et al., "Immobilization of polydiacetylene onto silica microbeads for colorimetric detection," J. Mater. Chem., 2006, 16, 546-549.

Norvez, S., et al., "Epitaxygens: mesomorphic properties of triptycene derivatives," Liquid Chemicals, 1993, vol. 14, No. 5, pp. 1389-1395.
Oda, Masao, et al., "Chiroptical properties of chiral-substituted polyfluorenes," Synthetic Metals, 2000, vol. 111-112, pp. 575-577.
Oda, Masao, et al., "Circularly Polarized Electroluminescence from Liquid-Crystalline Chiral Polyfluorenes," Advanced Materials, 2000, vol. 12, No. 5, pp. 362-365.
Office Action from U.S. Appl. No. 11/252,419 dated Dec. 12, 2008.
Office Action from U.S. Appl. No. 11/252,419 dated Jun. 12, 2009.
Office Action from U.S. Appl. No. 11/252,419 dated Mar. 13, 2008.
Okamoto, I. et al., "Orbital Unsymmetrization Affects Facial Selectivities of Diels-Alder Dienophiles," J. Org. Chem. 1996, 61, 3155-3166.
Ortega-Barrales et al., Solid-phase spectrophotometric determination of trace amounts of hydrazine at sub-ng ml-1 level. Anal Chim Acta. 1997;353:115-22.
Orynbayeva et al., Visualization of membrane processes in living cells by surface-attached chromatic polymer patches. Angew Chem Int Ed Engl. Feb. 4, 2005;44(7):1092-6.
Osborne et al., Nucleic Acid Selection and the Challenge of Combinatorial Chemistry. Chem Rev. Apr. 1, 1997;97(2):349-370.
Ow et al., "Bright and stable core-shell fluorescent silica nanoparticles," Nano Letters, 2005, 5(1), 113-117.
Park et al., "Ratiometric Optical PEBBLE Nanosensors for Real-Time Magnesium Ion Concentrations Inside Viable Cells," Anal. Chem., 2003, 75(15), 3784-3791.
Patel, et al., "Chemicapacitive microsensors for volatile organic compound detection," Sensors and Actuators B, 2003, 96, 541-553.
Peeters, Emiel, et al., "Circularly Polarized Electroluminescence from a Polymer Light-Emitting Diode," J. Am. Chem. Soc., 1997, vol. 119, No. 41, pp. 9909-9910.
Pei et al., First Hydrogen-Bonding-Induced Self-Assembled Aggregates of a Polyfluorene Derivative. Macromolecules. 2003;36:323-27.
Pei et al., Polymer Light-Emitting Electrochemical Cells: In Situ Formation of a Light-Emitting p-n Junction. J Am Chem Soc. 1996;118(16):3922-3929.
Peng, Kang-Yung, et al., "Efficient Light Harvesting by Sequential Energy Transfer across Aggregates in Polymers of Finite Conjugational Segments with Short Aliphatic Linkages," J. Am. Chem. Soc., 2001, vol. 123, pp. 11388-11397.
Perr et al., Solid phase microextraction ion mobility spectrometer interface for explosive and taggant detection. J Sep Sci. Feb. 2005;28(2):177-83.
Pingarron et al., Carbon fibre microelectrodes modified with rhodium for the electrocatalytic determination of hydrazine. Anal Chim Acta. 2001;439:281-90.
Pinnaduwage, et al., "Detection of 2,4-dinitrotoluene using microcantilever sensors," Sensors and Actuators B, 2004, 99, 223-229.
Pisarevskii et al., Fluoresence spectrum and quantum yield of DNA in solution. Zhurnal Prikladnoi Spektroskipii. 1966;5:621-24.
Place, Ileane, et al., "Stabilization of the Aggregation of Cyanine Dyes at the Molecular and Nanoscopic Level," Langmuir, Jul. 28, 2000, vol. 16, No. 23, pp. 9042-9048.
Pschirer, Neil G., et al., "Poly(fluorenyleneethynylene)s by Alkyne Metathesis: Optical Properties and Aggregation Behavior," Macromolecules, May 9, 2000, vol. 33, No. 11, pp. 3961-3963.
Ratcliffe, Polypyrrole-based sensor for hydrazine and ammonia. Anal Chim Acta. 1990;239:257-62.
Reddinger et al., "Electroactive π-Conjugated Polymers Based on Transition Metal-Containing Thiophenes Capable of Sensing Ionic and Neutral Species," ACS Polym. Prepr., 1997, 321-322.
Reddinger et al., "Electroactive π-Conjugated Polymers Based on Transition Metal-Containing Thiophenes," Synthetic Metals, 1997, 84:225-226.
Reddinger et al., "Tunable Redox and Optical Properties Using Transition Metal-Complexed Polythiophenes," Macromolecules, 1997, 30(3):673-675.
Rendina et al., "Oxidative Addition Reactions of Organplatinum (II) Complexes with Nitrogen-Donor Ligands," J. Chem. Rev. 1997, 1735-54.

(56) References Cited

OTHER PUBLICATIONS

Rininsland, F., et al., "High-throughput kinase assays with protein substrates using fluorescent polymer superquenching," BMC Biotechnology, vol. 5, No. 16 (2005). 6 pages.
Rininsland, F., et al., "Metal ion-mediated polymer superquenching for highly sensitive detection of kinase and phosphatase activities," PNAS, Oct. 26, 2004, 101(43): pp. 15295-15300.
Rose et al., "Excited-State Lifetime Modulation in Triphenylene-Based Conjugated Polymers," J. Am. Chem. Soc., 2001, 123:11298-11299.
Rose et al., Sensitivity gains in chemosensing by lasing action in organic polymers. Nature. Apr. 14, 2005;434(7035):876-9.
Sandrini et al., "Photochemistry of the Orthometalated cis-Bis[2-(2-thienyl)pyridine]platinum(II) Complex in Halocarbon Solvents," J. Am. Chem. Soc. 1987, 109, 7720-24.
Schwarz et al., "Spectroscopic Studies of Cyclometalated Platinum(II) Complexes: Optical Absorption and Emission of Single-Crystal cis-Bis(benzo[h]quinolinato)platinum(II)," Inorg. Chem. 1989, 28, 1053-59.
Segawa et al., "Approaches to conducting polymer devices with nano-structure: Electrochemical construction of one-dimensional and two-dimensional prophyrin-oligothiophene co=polymers," Synthetic Metals, 1995, 71:2151-2154.
Shabani et al., Indirect Spectrophotometric Determination of Trace Quantities of Hydrazine. Bull Korean Chem Soc. 2004;25:213-15.
Shamiryan, D. et al., "Low-k dielectric materials," Materials Today, Jan. 2004. 34-39.
Shimidzu et al., "Approaches to conducting polymer devices with nanostructures: photoelectrochemical function of one-dimensional and two-dimensional porphyrin polymers with oligothienyl molecular wire," Journal of Photochemistry and Photobiology A: Chemistry 99, 1995, Article 4168:1-7.
Smet, M. et al., "Synthesis of the Formal Diels-Alder Adducts of N-substituted Dehydromaleimides and Anthracene," Molecules 2000, 5, 179-188.
Snow A.W., et al., "Synthesis and Evaluation of Hexafluorodimethylcarbinol Functionalized Polymers as Microsensor Coatings," Journal of Applied Polymer Science, 1991, vol. 43, pp. 1659-1671.
Swager, Timothy M., "The Molecular Wire Approach to Sensory Signal Amplification," Acc. Chem. Res., 1998, vol. 31, No. 5, pp. 201-207.
Swager, Timothy M., et al., "Fluorescence Studies of Poly(p-phenyleneethynylene)s: The Effect of Anthracene Substitution," J. Phys .Chem., 1995, vol. 99, No. 14, pp. 4886-4893.
Tan, Chunyan, et al., "Photophysics, aggregation and amplified quenching of a water-soluble poly(phenylene ethynylene)," Chem. Commun., 2002, pp. 446-447.
Thomas, III et al. "Designing Amplifying Polymer Sensors for Explosives and Toxic Chemicals," Polymeric Materials: Science and Engineering 2006, 95, 81-82.
Thomas, III et al. "Trace Hydrazine Detection with Fluorescent Conjugated Polymers: A Turn-On Sensory Mechanism," Adv. Materials 2006, 18, 1047-1050.
Thomas, III et al., "Amplifying fluorescent polymer sensors for the explosives taggant 2,3- dimethyl-2,3-dinitrobutane (DMNB)," Chem. Commun. 2005, 4572-4574.
Thomas, III et al., "Conjugated Polymer Sensors: Design Principles Towards Enhanced Versatility," presented at the Army Science Conference, Dec. 2004.
Thomas, III et al., "Conjugated Polymer Sensors: Detection of DMNB and Hydrazine," presented at the Materials Research Symposium, Boston, MA (Dec. 2005).
Thomas, III et al., "Conjugated Polymer Sensors: Detection of DMNB and Hydrazine," presented to the American Chemical Society at the 230th National Meeting, Washington, D.C. (Aug. 28-Sep. 1, 2005).
Thomas, III et al., "Dark-Field Oxidative Addition-Based Chemosensing: New Bis-clyclometalated Pt(II) Complexes and Phosphorescent Detection of Cyanogen Halides," J. Am. Chem. Soc. 2006, 128, 16641-16648.
Thomas, III et al., "Synthesis and Optical Properties of Simple Amine-Containing Conjugated Polymers," Macromolecules, 2005, 38(7), 2716-2721.
Toal et al., Polymer sensors for nitroaromatic explosives detection. J Mater Chem. 2006;16:2871-83.
Treichel, H. et al., "Integration Challenges for Low Dielectric Constant Materials," Advanced Engineering Materials. 2001;7(3):461-64.
Tsai et al., New Thiophene-Linked Conjugated Poly(azomethine)s: Theoretical Electronic Structure, Synthesis, and Properties. Macromolecules. 2005;38:1958-66.
Van Houten, Kelly A., et al., "Rapid Luminescent Detection of Phosphate Esters in Solution and the Gas Phase Using (dppe)Pt{S2C2(2-pyridyl)(CH2CH2OH)}," J. Am. Chem. Soc., 1998, vol. 120, No. 47, pp. 12359-12360.
Vilas-Boas et al., "New Insights into the Structure and Properties of Electroactive Polymer Films Derived from [Ni(salen)]," Inorganic Chemistry, 1997, 36(22):4919-4929.
Virji et al., Hydrazine Detection by Polyaniline Using Fluorinated Alcohol Additives. Chem Mater. 2005;17(5):1256-1260.
Virji et al., Polyaniline Nanofiber Gas Sensors: Examination of Response Mechanisms. Nano Letters. 2004;4(3):491-496.
Von Zelewsky et al., "Thermal and Photochemical Oxidative Addition of Alkyl Halides to the Cyclometalated Complex cis-Bis[2-(2'-thienyl)pyridine]platinum(II)," Inorg. Chem. 1993, 32, 4585-93.
Walters, Keith A., et al., "Photophysical Consequences of Conformation and Aggregation in Dilute Solutions of π-Conjugated Oligomers," Langmuir, 1999, vol. 15, pp. 5676-5680.
Waluk, "Hydrogen-Bonding-Induced Phenomena in Bifunctional Heteroazaaromatics," Acc. Chem. Res. 2003, 36, 832-838.
Wang et al., Catalytic-adsorptive stripping voltammetric measurements of hydrazines. Talanta. Dec. 1988;35(12):965-8.
Wang et al., Hydrazine Detection Using a Tyrosinase-Based Inhibition Biosensor. Anal Chem. 1995;67:3824-27.
Wang, C., et al., "Biosensors from conjugated polyelectrolyte complexes," PNAS, 2002, 99(1): pp. 49-53.
Wang, D., et al. "Photoluminescence Quenching of Conjugated Macromolecules by Bipyridinium Derivatives in Aqueous Media: Charge Dependence,"Langmuir, 2001, 17(4): 1262-1266.
Wang, J., et al., "Photoluminescence of Water-Soluble Conjugated Polymers: Origin of Enhanced Quenching by Charge Transfer," Macromolecules 2000, 33(14):5153-5158.
Weder, Christoph, et al., "Efficient Solid-State Photoluminescence in New Poly(2,5-dialkoxy-p-phenyleneethynylene)s," Macromolecules, 1996, vol. 29, No. 15, pp. 5157-5165.
Whitten, D., et al., "From Superquenching to Biodetection: Building Sensors Based on Fluorescent Polyelectrolytes" Optical Sensors and Switches, pp. 189-208 (2001).
Willis et al., Fluoresence decay kinetics of tyrosinate and tyrosine hydrogen-bonded complexes. J Physical Chemistry 1991;95:1585-89.
Wolfbeis, "Materials for fluorescence-based optical chemical sensors," J. Mater. Chem., 2005, 15, 2657-2669.
Wosnick et al., "Layer-by-Layer Poly(phenylene ethynylene) Films on Silica Microspheres for Enhanced Sensory Amplification," Macromolecules, 2005, 38(22), 9287-9290.
Wosnick et al., "Synthesis and Application of Poly(phenylene Ethynylene)s for Bioconjugation: A Conjugated Polymer-Based Fluorogenic Probe for Proteases," J. Am. Chem. Soc., 2005, 127(10), 3400-3405.
Wu et al., "Preparation and Encapsulation of Highly Fluorescent Conjugated Polymer Nanoparticles," Langmuir, 2006, 22(7), 2956-2960.
Wu et al., Novel water-soluble fluorescent polymer containing recognition units: Synthesis and interactions with PC12 cell. Euro Polymer J. 2005;41:1985-1992.

(56) References Cited

OTHER PUBLICATIONS

Wu, Chi, et al., "Novel Nanoparticles Formed via Self-Assembly of Poly(ethylene glycol-b-sebacic anhydride) and Their Degradation in Water," Macromolecules, Oct. 31, 2000, vol. 33, No. 24, pp. 9040-9043.

Xia, et al., "A high-throughput screening assay for Kinases and Phosphatases via metal ion-mediated fluorescent polymer superquenching," American Laboratory, Oct. 2004, 36(20): pp. 15-19.

Xia, W., et al., "Applications of fluorescent polymer superquenching to high throughput screening assays for protein kinases," A&DDT, Apr. 2004, 2(2): pp. 183-192.

Yamaguchi et al., Light-emitting efficiency tuning of rod-shaped pi conjugated systems by donor and acceptor groups. J Am Chem Soc. Jul. 6, 2005;127(26):9332-3.

Yang et al.,Growth of Ultrathin Covalently Attached Polymer Films: Uniform Thin Films for Chemical Microsensors. Langmuir. 1998;14:1505-07.

Yang, Jye-Shane, et al., "Anomalous crystal packing of iptycene secondary diamides leading to novel chain and channel networks," Tetrahedron Letters, Oct. 7, 2000, vol. 41, Issue 41, pp. 7911-7915.

Yang, Jye-Shane, et al., "Fluorescent Porous Polymer Films as TNT Chemosensors: Electronic and Structural Effects," J. Am. Chem. Soc., 1998, vol. 120, No. 46, pp. 11864-11873.

Yang, Jye-Shane, et al., "Porous Shape Persistent Fluorescent Polymer Films: An Approach to TNT Sensory Materials," J. Am. Chem. Soc., Jun. 3, 1998, vol. 120, No. 21, pp. 5321-5322.

Yu et al., New efficient blue light emitting polymer for light emitting diodes. Chem Commun. 1999:1837-38.

Yuan et al., +Fiber optic chemical sensors using a modified conducting polymer cladding . SPIE. 2001;4205:170-79.

Zahn et al., "Three-Dimensional Electronic Delocalization in Chiral Conjugated Polymers," Angew. Chem. Int. Ed. Engl., 2002, 41(22):4226-4230.

Zhang et al., Fluorescent detection of chemical warfare agents: functional group specific ratiometric chemosensors. J Am Chem Soc. Mar. 26, 2003;125(12):3420-1.

Zhang, Guangzhao, et al., "Formation of Novel Polymeric Nanoparticles," Accounts of Chemical Research, Jan. 6, 2001, vol. 34, No. 3, pp. 249-256.

Zhao et al., "Sensory Responses in Solution vs Solid State: A Fluorescence Quenching Study of Poly(iptycenebutadiynylene)s," Macromolecules, 2005, 38(22), 9377-9384.

Zheng et al., Biotinylated poly(p-phenylene ethynylene): unexpected energy transfer results in the detection of biological analytes. Chem Commun (Camb). Dec. 21, 2004;(24):2798-9. Epub Nov. 4, 2004.

Zhou et al., Novel Polyphenylenes Containing Phenol-Substituted Oxadiazole Moieties as Fluorescent Chemosensors for Fluoride Ion. Macromolecules. 2005;38:2148-53.

Zhou, Qin, et al. "Fluorescent Chemosensors Based on Energy Migration in Conjugated Polymers: The Molecular Wire Approach to Increased Sensitivity," J. Am. Chem. Soc., 1995, vol. 117, No. 50, pp. 12593-12602.

Zhou, Qin, et al., "Methodology for Enhancing the Sensitivity of Fluorescent Chemosensors: Energy Migration in Conjugated Polymers," J. Am. Chem. Soc., 1995, vol. 117, No. 26 pp. 7017-7018.

Zhu et al., "Conducting Polymetallorotaxanes: A Supramolecular Approach to Transition Metal Ion Sensors," Journal of the American Chemical Society, 1996, 118(36):8713-8714.

Zhu et al., "Design of Conducting Redox Polymers: A Polythiophene-Ru(bipy)3n Hybrid Material," Adv. Mater., 1996, 8(6):497-500.

Zotti et al., "Conductivity in Redox Modified Conducting Polymers. 2. Enhanced Redox Conductivity in Ferrocene-Substituted Polypyrroles and Polythiophenes," Chem. Mater., 1995 7(12):2309-2315.

\* cited by examiner

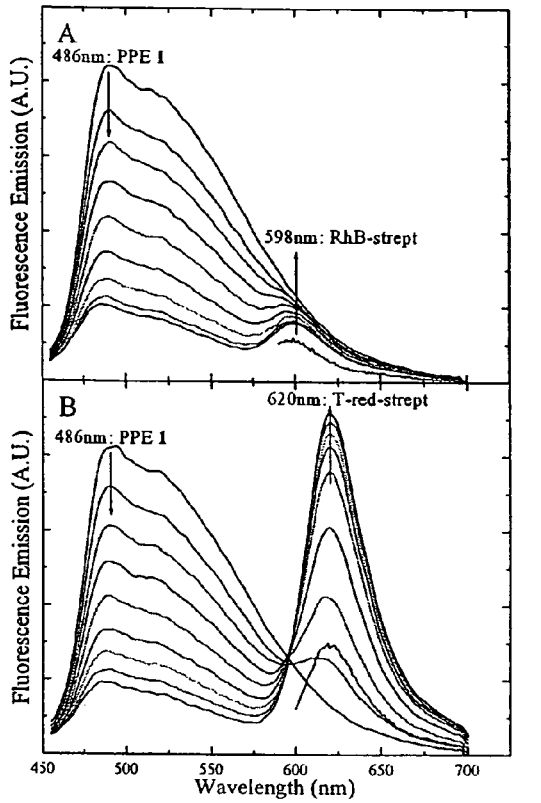
FIG. 3A
FIG. 3B
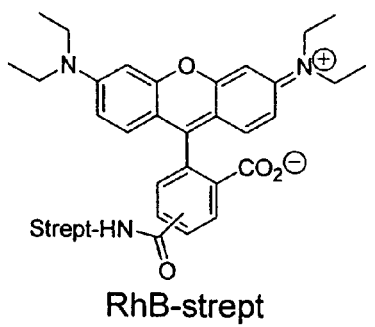
RhB-strept
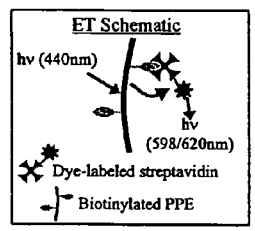
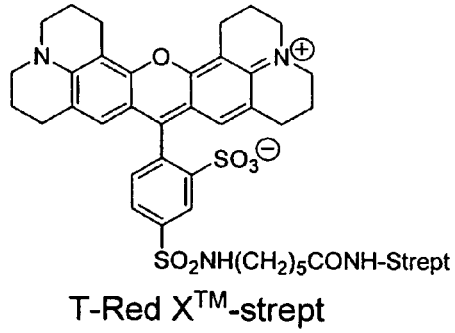
T-Red X™-strept
Figure 3C
Figure 3D
Figure 3E

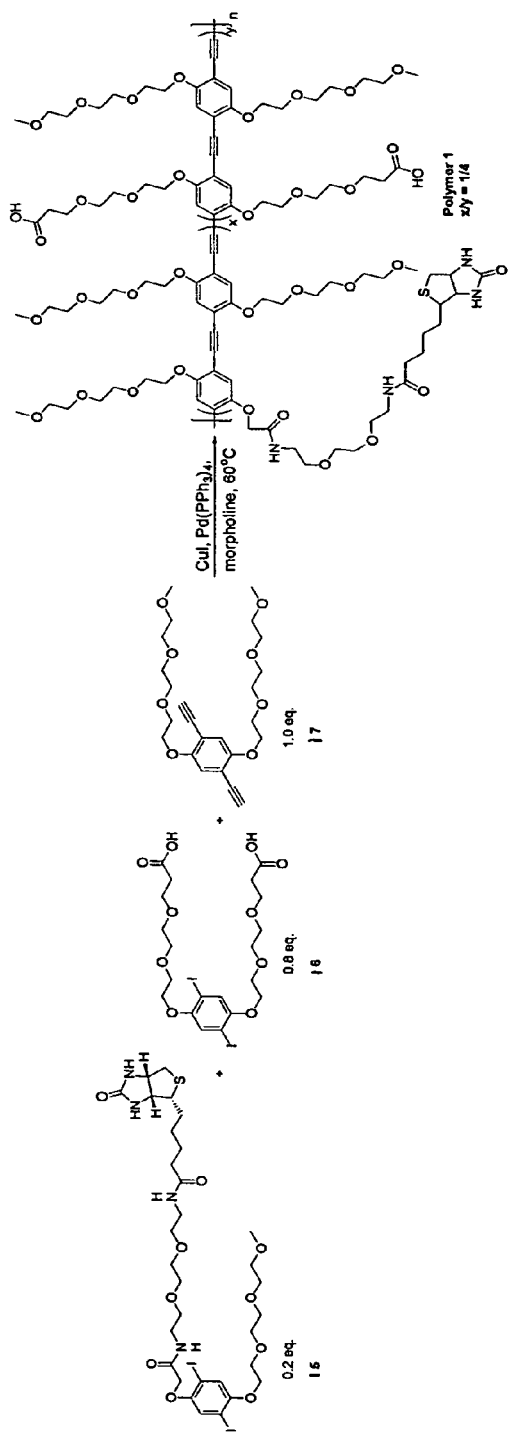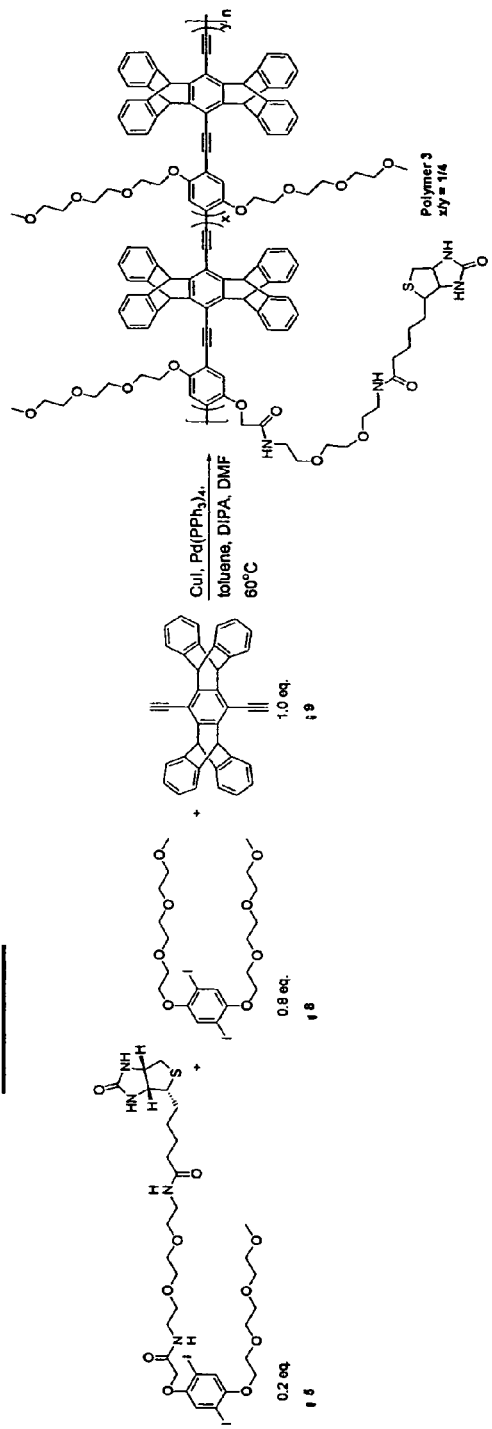
FIGURE 5B
FIGURE 5D

- 21 R=OH; x : y = 0 : 1
- 22a R = OH or NH(CH$_2$)$_2$OH; x : y = 1 : 1
  sugar = mannose
- 22b R = OH or NH(CH$_2$)$_2$OH; x : y = 1 : 1
  sugar = galactose Figure 8A
Figure 8B
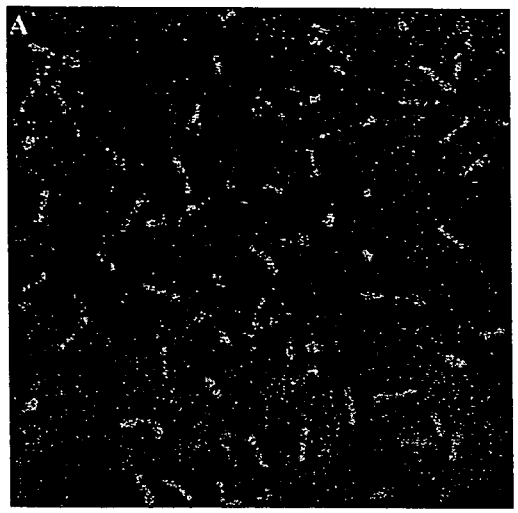
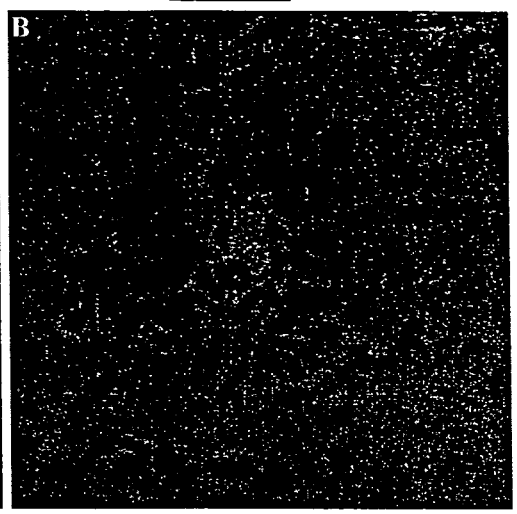
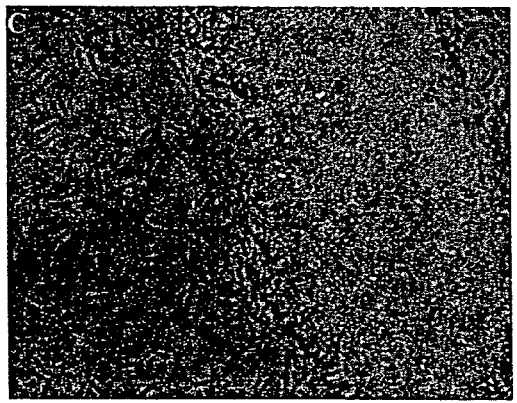
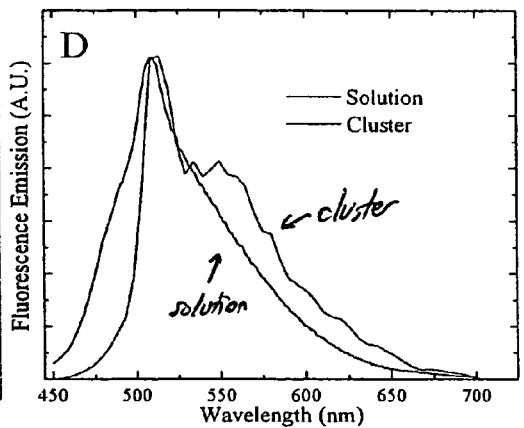
Figure 8C
Figure 8D

POLYMERS FOR ANALYTE DETECTION

RELATED APPLICATIONS

This application claims priority under 35 U.S.C. §119(e) to U.S. Provisional Application Ser. No. 60/610,743, entitled "POLYMERS FOR ANALYTE DETECTION," filed on Sep. 17, 2004, which is herein incorporated by reference in its entirety.

FEDERALLY SPONSORED RESEARCH

Various aspects of the research leading to the present invention were sponsored by NASA, Grant No. NAS2-02056. The Government may have certain rights in the invention.

FIELD OF INVENTION

The present invention generally relates to organic polymers and, in particular, to organic polymers able to participate in an analyte-recognition process.

BACKGROUND

Enterohemorrhagic *Escherichia coli* contaminated foods are a major cause of infection outbreaks with serious consequences. One of the largest outbreaks occurred in Japan in 1996, where over 10,000 people were infected and 11 died. Current detection methods for pathogenic bacteria such as *E. coil* rely on bacterial recognition using fluorescently labeled antibodies, DNA probes, or bacteriophages. While fluorescent conjugated polymers have found use in a variety of biological sensing applications, such as recognition of proteins by electrostatic interactions and detection of pathogens by DNA hybridization, the inventors know of no reported detection schemes for cells.

In many cases, pathogens bind to surface carbohydrates displayed on the cells they infect. A series of carbohydrate-pathogen interactions has been described, for example, *E. coli* binds to mannose, influenza virus binds to sialic acid, etc. The interactions of pathogens with cell surface carbohydrates are often multivalent, which results in higher binding affinity compared to monovalent binding.

SUMMARY OF THE INVENTION

The present invention generally relates to organic polymers able to participate in an analyte-recognition process. The subject matter of the present invention involves, in some cases, interrelated products, alternative solutions to a particular problem, and/or a plurality of different uses of one or more systems and/or articles.

In one aspect, the invention provides a method of determining an analyte. According to one set of embodiments, the method includes an act of exposing a sample suspected of containing an analyte to a polymer and an indicator. If the sample contains the analyte, then the analyte binds both the polymer and indicator in a manner bringing them into proximity with each other such that an emissive signal is produced at a threshold level. In some cases, the polymer and the indicator may be arranged with respect to each other, prior to the act of exposing, such that, in the absence of the analyte, the signal at the threshold level does not occur. In certain embodiments where the polymer is an energy donor and the indicator is an energy acceptor, each of the polymer and the indicator may have a maximum emission wavelength, where the maximum emission wavelength of the polymer and the maximum emission wavelength of the indicator are separated by at least about 100 nm. In some embodiments, the polymer and the indicator may be brought into proximity with each other via an interaction such as a ligand/receptor interaction. In particular embodiments, the polymer may be exposed to the indicator prior to or simultaneously with exposure of the polymer to the analyte. In some cases, the analyte is a biological entity capable of reproduction.

According to another set of embodiments, the method includes acts of exposing a sample suspected of containing a biological entity to a fluorescent conjugated polymer comprising a plurality of biological recognition elements, at least some of which are able to specifically interact with the biological entity, and determining fluorescence of the sample.

In yet another set of embodiments, the method is a method of determining a biological entity. The method includes steps of exposing a sample suspected of containing a biological entity to a fluorescent conjugated polymer capable of multivalent binding to a biological entity, and determining the biological entity by determining fluorescence of the sample. In still another set of embodiments, the method includes a step of specifically binding a fluorescent conjugated polymer to a biological entity.

Another aspect of the invention provides an article. The article, according to one set of embodiments, includes a fluorescent conjugated polymer comprising a plurality of biological recognition elements able to specifically interact with a biological entity. The article, according to another set of embodiments, includes a fluorescent conjugated polymer capable of multivalent binding to a biological entity. In yet another set of embodiments, the article includes a fluorescent conjugated polymer comprising a carbohydrate.

In another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures:

FIGS. 3A-3I illustrate spectral data of various polymers, in accordance with one embodiment of the invention;

FIGS. 5A-5E illustrate various reaction schemes useful for producing certain polymers of the invention;

FIGS. 8A-8D illustrate bacteria determined using another embodiment of the invention.

DETAILED DESCRIPTION

Figure 1:
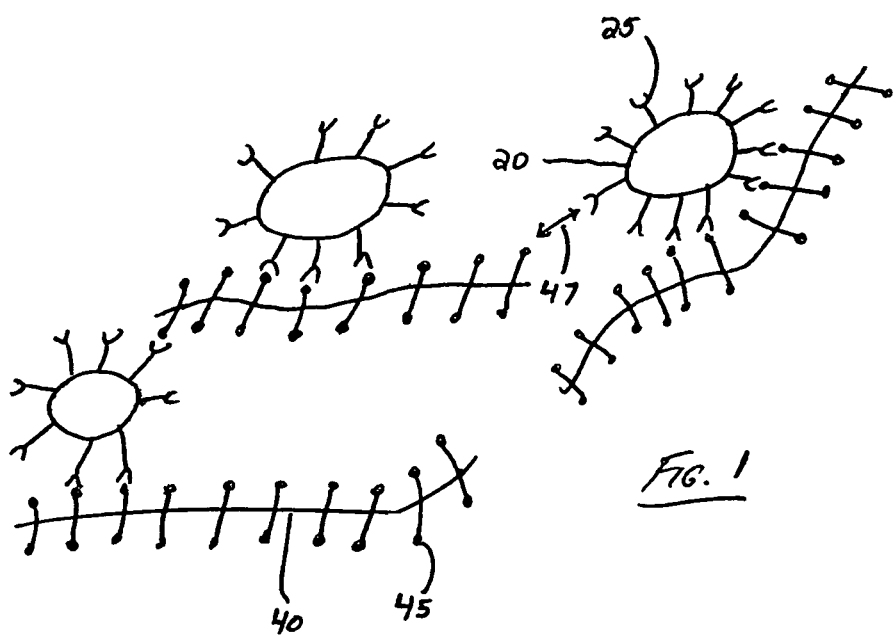
FIG. 1 is a schematic diagram illustrating multivalency, in accordance with one embodiment of the invention.

The present invention generally relates to organic polymers able to participate in an analyte-recognition process, where an analyte facilitates an energy transfer between an energy donor and an energy acceptor. Certain embodiments of the invention make use of fluorescent conjugated polymers, such as poly(phenylene ethynylene)s and other polymers comprising pi-conjugated backbones. For example, one aspect of the invention provides a fluorescent conjugated polymer and an indicator that can interact with each other in the presence of an analyte to produce an emissive signal. In some cases, the interaction may include energy exchange mechanisms, such as Dexter energy transfer or the strong coupling effect. The interaction of the conjugated polymer and the indicator, in some instances, may be facilitated through specific interactions, such as a protein/carbohydrate interaction, a ligand/receptor interaction, etc. Another aspect of the invention provides for the detection of biological entities, for example, pathogenic bacteria such as *E. coli*, or viruses such as influenza virus. In some cases, biological recognition elements may be used to determine the biological entity, for instance, carbohydrates that can be used to specifically interact with at least part of the biological entity, such as a protein in the cell membrane of a bacterium. Still other aspects of the invention involve articles, devices, and kits using any of the above-described systems.

The following applications are incorporated herein by reference: U.S. patent application Ser. No. 10/324,064, filed Dec. 18, 2002, entitled "Emissive Polymers and Devices Incorporating These Polymers," by Swager, et al., published as 2003-0178607 on Sep. 25, 2003; U.S. patent application Ser. No. 09/935,060, filed Aug. 21, 2001, entitled "Polymers with High Internal Free Volume," by Swager, et al., published as 2002-0150697 on Oct. 17, 2002; and U.S. patent application Ser. No. 10/621,041, filed Jul. 15, 2003, entitled "Emissive, High Charge Transport Polymers," by Swager, et al., published as 2004-0116650 on Jun. 17, 2004.

As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

Various aspects of the present invention include conjugated polymers that may be fluorescent. Polymers are generally extended molecular structures comprising backbones which optionally contain pendant side groups. As used herein, "backbone" is given its ordinary meaning as used in the art, e.g., a linear chain of atoms within the polymer molecule by which other chains may be regarded as being pendant. Typically, but not always, the backbone is the longest chain of atoms within the polymer.

A conjugated polymer is a polymer in which at least a portion of the polymer is conjugated, i.e. the polymer has at least one conjugated portion. "Conjugated," as used herein, refers to an interconnected chain of at least three atoms, each atom participating in delocalized pi-bonding. Electron density or electronic charge can be conducted along the conjugated portion of the polymer. Each p-orbital participating in conjugation may have sufficient overlap with adjacent conjugated p-orbitals. In one embodiment, the conjugated portion is at least about 3 nm in length. In another embodiment, the entire backbone may be conjugated. An example of a conjugated polymer is a polyacetylene chain. Other non-limiting examples include polyethylenes, poly(ethylene terephthalate)s, polyarylenes such as polyphenylenes, polythiophenes, polypyrroles, poly(arylene vinylene)s such as poly(phenylene vinylene)s, poly(arylene ethynylene)s such as poly(phenylene ethynylene)s, ladder polymers, etc., where "aryl" generally refers to an aromatic moiety, i.e., a moiety having at least one ring in which some electrons are delocalized in the ring. For instance, the aromatic moiety may include a benzene moiety, a naphthalenyl moiety, an anthracenyl moiety, a pyridinyl moiety, a furanyl moiety, etc. As used herein, a "ladder polymer" is a polymer having a backbone that cannot be severed without breaking at least two bonds. Co-polymers of these and/or other polymers are also polymers that can be used in the invention, for example, block, alternating, or random co-polymers, etc.

The conjugated polymer may have, in some cases, a chromophore that can absorb or emit electromagnetic radiation, for example, in the ultraviolet and/or visible range. For example, the chromophore may absorb energy, allowing the chromophore to achieve an excited state. The chromophore may also emit energy (e.g., as radiation) to achieve a lower energy state, and/or transmit energy through at least a portion of the conjugated polymer. Those of ordinary skill in the art will be able to identify the presence of a chromophore within a polymer. For instance, in one embodiment, the chromophore is a conjugated group. In another embodiment, the emitted radiation is created through luminescence, in which "luminescence" is defined as including ultraviolet and/or visible radiation. Specific types of luminescence include "fluorescence" and "phosphorescence." A chromophore able to fluoresce is also referred to herein as a "fluorophore." In some cases, the chromophore may have a maximum emission wavelength (i.e., the wavelength at the maximum intensity of the emission spectrum) greater than about 500 nm, greater than about 600 nm, greater than about 700 nm, or greater than about 800 nm. In some embodiments, the maximum emission wavelength may be between about 400 nm and about 700 nm, between about 300 nm and 700 nm, between about 400 nm and about 10 nm, etc. In some cases, the maximum emission wavelength may be between about 350 nm and about 1000 nm, between about 300 nm and about 500 nm, between about 500 nm and about 1 nm, between about 400 nm and about 700 nm, between about 600 nm and about 1000 nm, between about 500 nm and about 50 nm, etc. Those of ordinary skill in the art will be able to determine the emission (e.g., fluorescence, phosphorescence, etc.) of a polymer, for example, using known spectrofluorimetric techniques such as fluorometers, plate readers, fluorescence scanners, flow cytometers, fluorescence microscopes, etc.

A conjugated polymer may also allow energy transfer to occur along an "energy migration pathway" of the polymer, for example, a conjugated portion of the polymer. An energy migration pathway is a pathway which allows for the conduction of energy (i.e., without emission) away from a chromophore which has absorbed energy. The energy may be transferred, e.g., to another chromophore (e.g., a fluorophore) within the same polymer, and/or a chromophore of a different polymer located proximate the chromophore and/or the polymer comprising the chromophore. In some cases, an energy exchange mechanism, such as a Dexter energy transfer mechanism or the strong coupling effect, may facilitate energy transfer between a first chromophore on a first polymer and a second chromophore. The second chromophore may be, for example, present on the first polymer or present on a second polymer (which may be the same as or different than the first polymer), as further described below.

When a polymer includes conjugated portions, the polymer can, in some cases, undergo a phenomena known as "pi-stacking," which involves electron interactions between pi-orbitals of the conjugated portions of the same and/or different polymer molecules. If the polymer also includes a chromophore, a pi-stacking arrangement may also facilitate energy transfer between chromophores species.

In one set of embodiments, the conjugated polymer may interact with an indicator, i.e., a molecule or other moiety that is able to emit radiation upon interacting with the conjugated polymer. Typically, the indicator is or includes a chromophore or a fluorophore. For example, the indicator may be a commercially available indicator, for example, but not limited to, fluorescein, rhodamine B, Texas Red™ X, sulforhodamine, calcein, etc. In certain embodiments, the indicator itself may comprise a polymer. In some cases, interaction between the indicator and the polymer may be facilitated by the presence of an analyte, as further discussed below. In some cases, the interaction between the indicator and the conjugated polymer may also alter the emission of the conjugated polymer, e.g., if the polymer also comprises a chromophore or a fluorophore. In some cases, the conjugated polymer and the indicator may interact through an energy exchange mechanism, such as a Dexter energy transfer mechanism or the strong coupling effect.

In some cases, the indicator may be chosen such that the emission of the indicator does not have a high degree of spectral overlap with the emission of the conjugated polymer, as further discussed below. Thus, the indicator may be chosen to reduce stray light (background) emissions, which may lead to increased sensitivity and more sensitive sensors in various embodiments of the invention.

Various embodiments of the invention provide for the transfer of energy from a first chromophore (an energy donor) to a second chromophore (an energy acceptor). For example, energy may be transferred along a conjugated polymer between a first chromophore of the conjugated polymer and a second chromophore of the conjugated polymer, between a chromophore on a conjugated polymer and an indicator (which may be attached to or separated from the conjugated polymer), between multiple indicators, etc. In some cases, energy within a specific range (i.e., an energy band) may be transferred between the first chromophore and the second chromophore.

In some embodiments, the first chromophore and the second chromophore may interact through an energy exchange mechanism, such as a Dexter energy transfer mechanism or the strong coupling effect. In certain embodiments of the invention, the energy exchange may occur without the substantial involvement of the well-known Förster mechanism. Such energy transfer mechanisms may be determined, for example, by exciting the chromophores at their maximum absorbance (e.g., at a wavelength or frequency where the polymer does not significantly absorb the exciting radiation), measuring quantum yield, and comparing the yield to predicted values. An example of such a technique is discussed in Example 1.

Energy transfer between the first chromophore and the second chromophore may occur due to the strong coupling effect in some cases, where the chromophores interact to give a common quantum mechanical state, i.e., where the molecules containing the chromophores are close enough to create substantial or non-negligible overlap between their respective molecular wave functions. As an example, an energy donor such as a conjugated polymer may be positioned in proximity with an energy acceptor such as an indicator, for instance, due to the presence of an analyte. Thus, in one set of embodiments, two or more chromophores (e.g., an energy donor and an energy acceptor) may be brought into proximity such that energy transfer may occur between the chromophores through such an energy exchange mechanism. For example, two or more chromophores may be brought to within about 10 nm of each other, and in some cases, such that the chromophores are within about 5 nm of each other, within about 3 nm of each other, within about 2 nm of each other, or within about 1 nm of each other or less. In some cases, as further discussed below, the two or more chromophores may be brought in proximity with each other using specific interactions, such as protein/carbohydrate, ligand/receptor (e.g., biotin/avidin or biotin/streptavidin), etc. In certain instances, the transfer of energy through the polymer is highly distance dependent. Thus, distances between chromophores may be determined, for example, by determining the intensity of light emission.

Certain embodiments of the invention provide for the transfer of energy from an energy donor (e.g., a conjugated polymer) to an energy acceptor (e.g., an indicator) without the need for spectral overlap between the energy donor and the energy acceptor, i.e., such that the emission spectrum of the energy donor does not necessarily significantly overlap the spectrum absorption spectrum of the energy acceptor. As used herein, "spectral overlap" is given its ordinary meaning as used in the art, i.e., when two spectra are normalized and superimposed, an area exists that is simultaneously under both curves (i.e., as determined by integrals). In one embodiment of the invention, this spectral overlap is less than about 25% of the total combined area of both curves. Minimized spectral overlap is desired, but not required, and in some cases, the overlap between the two spectra may be less than about 20%, less than about 15%, less than about 10%, less than about 5%, less than about 3%, less than about 1%, less than about 0.3%, less than about 0.1%, less than about 0.03%, or less than about 0.01% or less. In certain cases, though, there may still be some overlap between both spectra, for example, an overlap of at least about 0.1%, at least about 0.3%, at least about 1%, at least about 5%, at least about 10%, at least about 15%, etc.

In another set of embodiments, the first chromophore may have a first emission lifetime and the second chromophore may have a second emission lifetime at least about 5 times greater than the first emission lifetime, and in some cases, at least about 10 times greater, at least about 15 times greater, at least about 20 times greater, at least about 25 times greater, at least about 35 times greater, at least about 50 times greater, at least about 75 times greater, at least about 100 times greater, at least about 125 times greater, at least about 150 times greater, at least about 200 times greater, at least about 250 times greater, at least about 350 times greater, at least about 500 times greater, etc.

In yet another set of embodiments, the second chromophore may enhance emission of the first chromophore, for example, by a factor of at least about 5-fold, at least about 10-fold, at least about 30-fold, at least about 100-fold, at least about 300-fold, at least about 1000-fold, at least about 3000-fold, or at least about 10,000-fold or more in some cases.

If the energy transfer includes Förster transfer, then the energy transfer may advantageously be enhanced by larger spectral overlap, according to another embodiment of the invention. That is, energy may be transferred from the first chromophore (e.g., an energy donor, such a fluorescent polymer) to the second chromophore (e.g., an energy acceptor, such as an indicator) through Förster transfer, a Dexter mechanism, or a combination of Förster transfer and a Dexter mechanism. In cases where the energy transfer can occur by a Dexter mechanism, then the amount of energy transfer will be substantially independent of the spectral overlap between the first chromophore to the second chromophore, unlike situations in which Förster transfer is the only mechanism of energy transfer between the first chromophore and the second chromophore, where the degree of energy transfer varies with the amount of spectral overlap between the first and second chromophores. Thus, in one set of embodiments, the mechanism of energy transfer between a first chromophore and a second chromophore (e.g., Dexter vs. Förster) can be determined by determining the amount that energy transfer between the first and second chromophores is enhanced by the spectral overlap. Reduced spectral overlap may allow the energy transfer to give rise to new threshold emissions in the presence of the analyte, where the new threshold emissions have minimal overlap with emissions in the absence of analyte.

In one set of embodiments, the new threshold emission may have a peak maximum of at least about 100 nm higher in wavelength than that of the dominant non-threshold emission, i.e., the first chromophore (e.g., an energy donor) and the second chromophore (e.g., an energy acceptor) may have maximum emission wavelengths that differ by at least about 100 nm. In other cases, the new threshold emission may have a peak maximum of at least about 150 nm higher in wavelength than that of the dominant non-threshold emission. In yet other cases, the new threshold emission may have a peak maximum of at least about 200 nm, about 250 nm, about 300 nm, or more higher in wavelength than that of the dominant non-threshold emission.

Energy exchange mechanisms, in some embodiments, may also enhance spatial sensitivity, allowing the use of systems and methods that cannot be performed using only conventional techniques, for example, FRET techniques (fluorescence resonance energy transfer techniques). For example, enzymes or proteins may undergo conformational changes upon binding a biomolecule or other analyte. These conformational changes can result in small changes in the positions of respective functionality of the enzyme or protein. However, as small changes in conformation can significantly reduce orbital interactions and thereby reduce or alter energy transfer between an energy donor and an energy acceptor, the systems and methods of the present invention can allow for the determination of changes in conformation of the enzyme or protein. For example, a change in conformation of an enzyme or a protein may increase or decrease energy transfer between an energy donor (e.g., a fluorescent polymer) and an energy acceptor (e.g., an indicator), which may be detected in some fashion, for example, by detecting an increase or decrease in emission from the indicator, detecting a change in the peak maximum of the emission of the indicator, etc. Thus, certain embodiments of the present invention provide for the determination of allosteric-type binding events, for example, to determine the role of proteases, co-factors, small molecules, etc., or selective hybridization events involving DNA, RNA, etc.

In some aspects of the invention, two or more chromophores may be brought in proximity with each other using specific interactions. For example, an analyte may cause a polymer (e.g., a conjugated polymer) and an indicator to be brought into proximity, such that a first chromophore on the polymer and a second chromophore on the indicator can participate in energy transfer, as described above. Thus, for instance, a polymer may comprise a ligand and the indicator may comprise a receptor to that ligand, the polymer may comprise biotin and the indicator may comprise avidin or streptavidin, the polymer may comprise an oligonucleotide (DNA and/or RNA) and the indicator may comprise a substantially complementary oligonucleotide, etc.

As used herein, "binding" can involve any hydrophobic, non-specific, or specific interaction, and the term "biological binding" refers to the interaction between a corresponding pair of molecules that exhibit mutual affinity or binding capacity, typically specific or non-specific binding or interaction. Biological binding defines a type of interaction that occurs between pairs of molecules including proteins, nucleic acids, glycoproteins, carbohydrates, hormones, and the like. Specific examples include protein/carbohydrate, antibody/antigen, antibody/hapten, biotin/streptavidin, biotin/avidin, enzyme/substrate, enzyme/inhibitor, enzyme/cofactor, protein/substrate, lectin/carbohydrate, receptor/hormone, receptor/effector, complementary strands of nucleic acid (e.g., DNA and/or RNA), protein/nucleic acid, repressor/inducer, ligand/receptor, virus/ligand, etc. Further, the term "binding partner" refers to a molecule that can undergo binding with a particular molecule. "Specific interaction" is given its ordinary meaning as used in the art, i.e., an interaction between pairs of molecules where the molecules have a higher recognition or affinity for each other than for other, dissimilar molecules. Biotin/avidin and biotin/streptavidin are examples of specific interactions. In some cases, the specific interaction involves uncharged molecules or neutral ligands.

In one set of embodiments, the presence of an analyte may facilitate bringing the chromophores on the polymer and the indicator into proximity. Thus, by analyzing emission of one or more of the chromophores, the presence of the analyte, and/or the concentration of the analyte, may be determined. As an example, the analyte may specifically bind to the first chromophore (e.g., a conjugated polymer) and to the second chromophore (e.g., an indicator), the analyte may catalyze a reaction that allows the two chromophores to interact (e.g., the analyte may include an enzyme, as discussed below), etc. The analyte, the first chromophore, and the second chromophore may interact in any order, so long as the chromophores are brought into proximity with each other. For example, the first chromophore (e.g., a conjugated polymer) and the analyte may first interact, then the second chromophore (e.g., an indicator) may interact with one or both of the first chromophore and the analyte; the first chromophore (e.g., a conjugated polymer) and the second chromophore (e.g., an indicator) may first interact, then one or both chromophores may interact with an analyte; the analyte, the first chromophore, and the second chromophore may all simultaneously interact; or the like. Interaction of the first and/or, second chromophores with the analyte may give a emission having a threshold level that, in the absence of the analyte, the first and/or second chromophores do not produce an emission that is at or above the emission threshold level.

In one set of embodiments, the analyte may include an enzyme or other species that is able to affect the interaction between the chromophores, e.g., of the polymer and the indicator. For example, an enzyme or other species may be able to alter the emission and/or absorption of light from a chromophore (e.g., a fluorophore), for instance, when manipulated (e.g., activated, reacted, etc.) in some fashion. Thus, in some embodiments, an enzyme may produce a product that alters the emission and/or absorption of the chromophore. For example, an enzyme may produce a product that enhances or inhibits emission or absorption of the chromophore or fluorophore of a conjugated polymer. The enzymatic product may be a chromophore in some cases, e.g., that is able to transfer energy to and/or from the conjugated polymer through energy exchange mechanisms such as those described herein. As another example, the enzymatic product may be an agent able to interfere with an interaction between the chromophore and the analyte, and/or an agent able to interfere with an interaction between two or more chromophores. For instance, the enzymatic product may cause dissociation to occur, compete with the interaction (e.g., competitive binding, noncompetitive binding, etc.), or the like, which may cause an alteration in the emission or absorption of at least one of the chromophores. As yet another example, the enzymatic product may be an agent able to at least partially quench emission from at least one of the chromophores. For instance, the enzymatic product may be a nitroaromatic moiety (i.e., an aromatic moiety comprising at least one nitro group) that alters emission of a chromophore or fluorophore.

One aspect of the invention provides systems and methods for determining a biological entity in a sample, for example, determining the presence, type, amount, etc. of the biological entity within a sample. A sample may be exposed to one or more of the polymers described herein, for example, including conjugated polymers comprising chromophores and/or biological recognition elements, conjugated polymers capable of multivalent binding, etc. If the conjugated polymer comprises a chromophore such as a fluorophore, the emission or absorbance (e.g., fluorescence, phosphorescence, etc.) of the conjugated polymer may then be determined to determine the biological entity. For instance, the biological entity may facilitate an interaction between the conjugated polymer comprising the chromophore and an indicator that can be determined to determine the biological entity. The sample may be taken from any suitable source where the presence of the biological entity is to be determined, for example, from food, water, plants, animals, bodily fluids (for example lymph, saliva, blood, urine, milk and breast secretions, etc.), tissue samples, environmental samples (for example, air, water, soil, plants, animals, etc.), or the like. In one embodiment, the biological entity is a pathogen.

As used herein, a "biological entity," is an entity deriving at least partially from a biological source. Non-limiting examples of biological entities include proteins, peptides, nucleic acids (e.g., oligonucleotides, which may include DNA and/or RNA), fatty acids, carbohydrates, sugars, hormones, enzymes, receptors, lipids, viruses, bacteria, cells, and the like. In some cases, the biological entity has the capability for reproduction, which can be self-reproduction, i.e., a biological entity is a cell (e.g., a bacterium) or a virus. In certain cases, the biological entity is a "pathogen," i.e., an entity capable of causing a disease when introduced into a subject, for example, a human, a dog, a cat, a horse, a cow, a pig, a sheep, a goat, a chicken, a primate, a rat, a mouse, etc.

In one set of embodiments, certain conjugated polymers of the invention include one or more biological recognition elements, for example, covalently attached to the polymer. If the conjugated polymer comprises a chromophore or a fluorophore, in some cases, the emission of the chromophore or fluorophore may change upon the interaction of the biological recognition element with the biological entity. In other cases, however, the emission of the chromophore or fluorophore may be unchanged upon such interaction, i.e., the chromophore or fluorophore acts as a "label" of the biological entity.

As used herein, a "biological recognition element" is an entity able to interact with the biological entity and/or a species present on a biological entity, such as a bacterium, a cell, a virus, etc, for example, by specifically binding to the species. In some cases, the interaction may be a specific interaction. For example, the entity may interact with the species such that the entity has an affinity to the species greater than the affinity of the entity to other species present on the biological entity, or present on similar biological entities. For instance, the biological recognition element may interact with a protein expressed on the surface of a bacterium or a cell, e.g., by binding to the protein, while the biological recognition element does not interact (and/or interacts with less affinity) to other, similar proteins present on the bacterium or cell and/or other bacteria or cells.

In certain cases, the biological recognition element specifically interacts with the biological entity, i.e., the biological recognition element interacts with a particular biological entity (or biological entity type), to a significantly greater degree than to other biological entity. For example, if the biological entity is a *Escherichia coli*, then the biological recognition element may specifically bind to *Escherichia coli* to a significantly greater degree than to other *Escherichia* species, to other bacteria, etc.

Non-limiting examples of species that may be present on a biological entity include proteins, for example, a cell surface receptor, an enzyme, a structural protein, etc. Other examples include certain receptors and lipids, for instance, phospholipids. An example of a biological recognition element are carbohydrates, for instance, which may specifically bind a protein on the surface of a bacterium or a cell. Examples of carbohydrates include monosaccharides, oligosaccharides, and polysaccharides. Other, non-limiting examples of biological recognition elements include glycosaminoglycans, glycolipids, proteins, antibodies, glycoproteins, and lectins (i.e., glycoproteins able to bind carbohydrates, in some cases, resulting in cell agglomeration). Additional, non-limiting examples of carbohydrates able to bind to biological entities include mannose (which is able to bind *Escherichia coli* or *Salmonella entrica*), fucose (which is able to bind *Psuedomonas aerginosa*), sialic acid (which is able to bind the influenza virus), heparin (which is able to bind herpes simplex virus), or the Lewis group antigens (which are able to bind *Helicobacter pylori*). In many cases, these interactions are multivalent in nature. In some cases, the carbohydrate may be specifically chosen to bind to a certain biological entity. Non-limiting examples of such carbohydrates include those discussed in D. M. Ratner, et al., "Probing Protein-Carbohydrate Interactions with Microarrays of Synthetic Oligosaccharides," *Chem Bio Chem*, 5:379-383, 2004, incorporated herein by reference.

As used herein, a "carbohydrate" (or, equivalently, a "sugar") is a saccharide (including monosaccharides, oligosaccharides and polysaccharides) and/or a molecule (including oligomers or polymers) derived from one or more monosaccharides, e.g., by reduction of carbonyl groups, by oxidation of one or more terminal groups to carboxylic acids, by replacement of one or more hydroxy group(s) by a hydrogen atom, an amino group, a thiol group or similar heteroatomic groups, etc. The term "carbohydrate" also includes derivatives of these compounds. Non-limiting examples of carbohydrates include allose ("All"), altrose ("Alt"), arabinose ("Ara"), erythrose, erythrulose, fructose ("Fru"), fucosamine ("FucN"), fucose ("Fuc"), galactosamine ("GalN"), galactose ("Gal"), glucosamine ("GlcN"), glucosaminitol ("GlcN-ol"), glucose ("Glc"), glyceraldehyde, 2,3-dihydroxypropanal, glycerol ("Gro"), propane-1,2,3-triol, glycerone ("1,3-dihydroxyacetone"), 1,3-dihydroxypropanone, gulose ("Gul"), idose ("Ido"), lyxose ("Lyx"), mannosamine ("ManN"), mannose ("Man"), psicose ("Psi"), quinovose ("Qui"), quinovosamine, rhamnitol ("Rha-ol"), rhamnosamine ("RhaN"), rhamnose ("Rha"), ribose ("Rib"), ribulose ("Rul"), sorbose ("Sor"), tagatose ("Tag"), talose ("Tal"), tartaric acid, erythraric/threaric acid, threose, xylose ("Xyl"), or xylulose ("Xul"). In some cases, the carbohydrate may be a pentose (i.e., having 5 carbons) or a hexose (i.e., having 6 carbons); and in certain instances, the carbohydrate may be an oligosaccharide comprising pentose and/or hexose units, e.g., including those described above. A "monosaccharide," is a carbohydrate or carbohydrate derivative that includes one saccharide unit. Similarly, a "disaccharide," a "trisaccharide," a "tetrasaccharide," a "pentasaccharide," etc. respectively has 2, 3, 4, 5, etc. saccharide units. An "oligosaccharide," as used herein, has 1-20 saccharide units, and the saccharide units may be joined in any suitable configuration, for example, through alpha or beta linkages, using any suitable hydroxy moiety, etc. The oligosaccharide may be linear, or branched in certain instances. A "polysaccharide," as used herein, typically has at least 20 saccharide units. For instance, the polysaccharide may have at least 25 saccharide units, at least 50 saccharide units, at least 75 saccharide units, at least 100 saccharide units, etc. In some cases, the carbohydrate is multimeric, i.e., comprising more than one saccharide chain.

In some cases, the conjugated polymers comprising biological recognition elements are durable, and can be stored for extended periods of time (weeks to months or years), and/or at room temperature (about 25° C.) and/or near room temperatures (i.e., between about 4° C. and about 25° C.), without denaturing (unlike proteins or antibodies) or decomposing. In some cases, even higher temperatures (i.e., greater than room temperature) may be used.

In one set of embodiments, the polymer may comprise a structure:

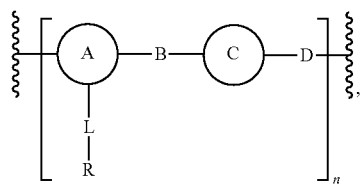

where n is at least 1, A and C are each aromatic moieties, and B and D are each independently selected from the group consisting of a carbon-carbon double bond

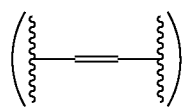

and a carbon-carbon triple bond

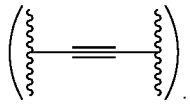

In some cases, n is less than 10,000. In one embodiment, one or both of A and C is a benzene ring, a triptycene moiety, or a pentiptycene moiety. Each of A and C may optionally comprise one or more pendant groups, for example, ethylene glycol units (as discussed below), which may be terminated by moieties such as alkyls (e.g., $-CH_3$), $-(CH_2)_p-CH_3$ (p being a positive integer), $-OH$, $-NH-CH_2-CH_2-OH$, $-CH_2-CH_2-COOH$, $-CH_2-CH_2-CO-NH-CH_2-CH_2-OH$, $-O-CH_2-CO-NH_2$, $-CH_2-CH_2-NH_2$ etc. In the above structure, R is a biological recognition element, for example, a carbohydrate, biotin, a protein, etc. For example, in one embodiment, R comprises a structure:

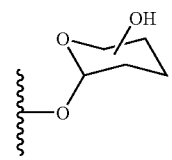

In another embodiment, R comprises one or more nucleic acids, e.g., DNA or RNA. For instance, R may comprise an oligonucleotide, for example, having at least 2 nucleotides, and in some cases, the polymer may have at least 5 nucleotides, at least 8 nucleotides, at least 10 nucleotides, at least 15 nucleotides, etc. Those of ordinary skill in the art will recognize that an "oligonucleotide" is not precisely defined in terms of the number of bases present within the nucleotide sequence. In some cases, the oligonucleotide may have about 20 bases or less.

Additionally, L is a moiety connecting A to R. L can comprise, for example, one or more ethylene glycol units, i.e.:

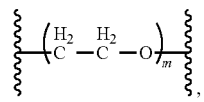

where m is at least 1. For example, m can be, inclusively, 1 to 15, 1 to 10, 1 to 7, 1 to 5, 1 to 3, 1 to 2, etc. In some cases, L may also comprise other linkages, for example, $-CO-NH-$, $-CH_2-$, $-(CH_2)_p-$ (p being a positive integer), $-NH-CH_2-CH_2-$, $-CH_2-CH_2-CO-$, $-CH_2-CH_2-CO-NH-CH_2-CH_2-$, $-O-CH_2-CO-NH-$, $-CH_2-CH_2-NH-$, etc. Any number of linkages such as these may be present (including duplications), and the linkages may appear in order connecting A to R. Examples of such structures may be seen in FIGS. 2A-2B and FIG. 6.

As used herein in reference to various chemical structures, the symbol "⌇" as is understood by those of ordinary skill in the art, indicates a point of attachment of a chemical structure to another chemical structure.

In one embodiment, the polymer comprises a structure:

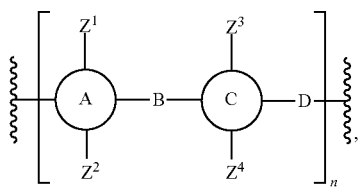

where n is at least 1, A and C are each aromatic moieties, and B and D are each independently selected from the group consisting of a carbon-carbon double bond

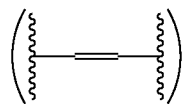

and a carbon-carbon triple bond

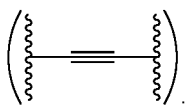

One or more of $Z^1$, $Z^2$, $Z^3$, and $Z^4$ may comprise a biological recognition element, for example, a carbohydrate, biotin, a protein, etc. In some cases, one or more of $Z^1$, $Z^2$, $Z^3$, and $Z^4$ each independently comprises one or more ethylene glycol units.

In another embodiment, the polymer comprises a structure:

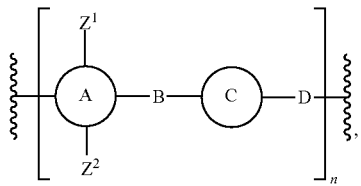

where n is at least 1, A is an aromatic moiety, C is a pentiptycene moiety, and B and D are each independently selected from the group consisting of a carbon-carbon double bond

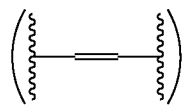

and a carbon-carbon triple bond

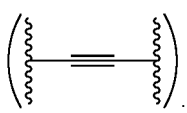

One or both of $Z^1$ and $Z^2$ may comprise a biological recognition element, for example, a carbohydrate, biotin, a protein, etc. In some cases, one or both of $Z^1$ and $Z^2$ independently comprises one or more ethylene glycol units.

Another aspect of the invention generally relates to conjugated polymers capable of multivalent binding. As used herein, a polymer is "multivalent" with respect to a species if the polymer is capable of being bound, simultaneously, at more than one location within the polymer, to one or more species. For example, more than one carbohydrate moiety on a conjugated polymer may be able to simultaneously bind to multiple proteins on a biological entity, more than one biotin moiety on a conjugated polymer may be able to simultaneously bind to an avidin or a streptavidin, etc. In some cases, ligands capable of multivalent binding may be covalently bonded to a conjugated polymer.

In certain embodiments, multiple conjugated polymers, each comprising one or more carbohydrates, may each become bound to proteins present on a bacterium or a cell. As an example, a biological entity may be exposed to a first conjugated polymer that is fluorescent and/or comprises one or more biological recognition elements, and a second conjugated polymer that is also fluorescent and/or comprises one or more biological recognition elements. The first and second conjugated polymers may have similar structures (for example, having the same backbone and/or biological recognition elements), or different structures (for example, different biological recognition elements). Typically, in reference to biological systems, multivalent binding is stronger and more selective relative to monovalent binding.

In some embodiments, multivalent binding of ligands may give rise to agglomerated structures. If polymers are associated with the ligands, the polymers may thus be brought proximate to each other, for instance, such that an energy exchange mechanism, such as a Dexter energy transfer mechanism or the strong coupling effect, may facilitate energy transfer between at least some of the agglomerated polymers, as described above.

An example of multivalent binding can be seen in FIG. 1, where a plurality of polymers 40 each containing a plurality of carbohydrates or other biological recognition elements 45 has been exposed to a series of cells 20 (for example, bacteria or other pathogens). The carbohydrates or other biological recognition elements 45 are able to recognize a species 25 on the cells (as indicated by arrow 47). Due to their multivalency, the polymers may bind to more than one cell, which may cause agglomeration of the cells to occur.

In still another aspect of the invention, kits are provided, containing one or more of the above-described compositions of the invention. A "kit," as used herein, typically defines a package or an assembly including one or more of the compositions of the invention, and/or other compositions associated with the invention, for example, as previously described. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, modifying, assembling, storing, packaging, preparing, mixing, diluting, and/or preserving the compositions components for a particular use, for example, to a sample.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, assembly, storage, packaging, and/or preparation of the compositions and/or other compositions associated with the kit. In some cases, the instructions may also include instructions for the delivery of the compositions, for example, for a particular use, e.g., to a sample. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

Yet another aspect of the invention provides for the promotion of any of the above-described compositions, kits, or methods of the invention. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, or the like that are associated with the systems, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following examples are intended to illustrate certain embodiments of the present invention, but do not exemplify the full scope of the invention.

Example 1

In recent years, the fluorescence properties of conjugated polymers ("CPs") have been investigated in the design of chemical and biological sensors, the majority of which have been based upon the amplification of fluorescence quenching. In contrast to turn-off sensors, a turn-on sensor using fluorescence resonance energy transfer ("FRET") with CPs as light-harvesting donors has the advantage of being more sensitive and selective. Although FRET is widely used in biology to study biomolecular structure and dynamics, its use with CPs as a method of transduction for sensing biological molecules is not common. This example illustrates studies between biotinylated poly(p-phenylene ethynylene) ("PPE") and fluorophore-labeled streptavidin. This example reveals that, unexpectedly, energy transfer in such a system is not governed by a typical Förster mechanism.

Figure 2A:
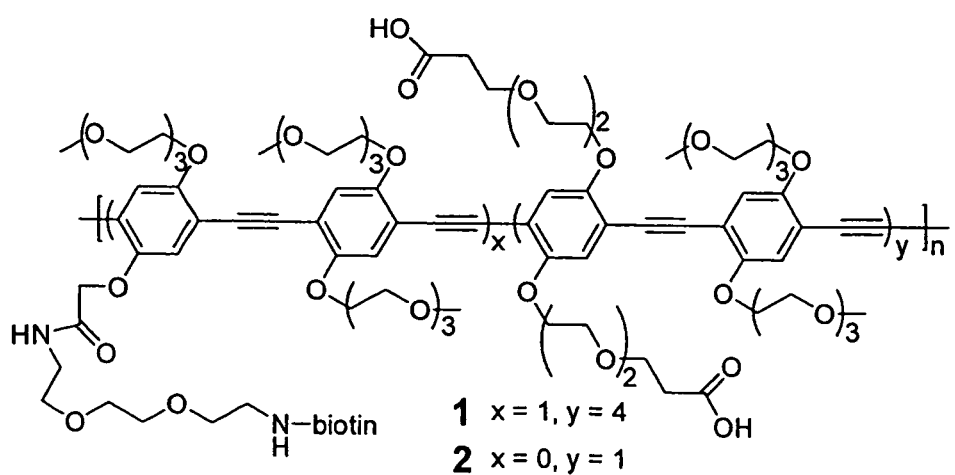
FIGS. 2A-2B illustrates certain polymers in accordance with various embodiments of the invention.
Figure 2B:
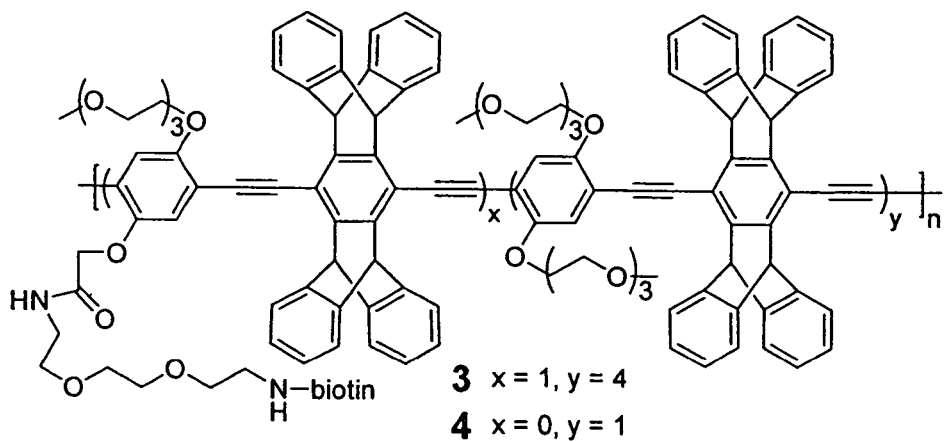

Streptavidin is a tetrameric protein that binds up to four molecules of d-biotin with a dissociation constant estimated to be about $4 \times 10^{-14}$ M. Because of this relatively high affinity, the streptavidin-biotin recognition system can be used in biosensor design, in conjunction with conjugated polymers in affinity-chromic and/or agglutination assays. A water-soluble biotinylated PPE 1 and its non-biotinylated relative 2 were synthesized for solution energy transfer ("ET") experiments via a Sonagashira-Hagihara cross-coupling reaction. These polymers are shown in FIG. 2A. Analogously, an organic solvent-soluble biotinylated PPE 3 and its non-biotinylated variation 4 for solid phase thin-film experiments were also synthesized. These are illustrated in FIG. 2B. A schematic view of the experiments is shown in FIG. 3D.

Polymer 1 was constructed from two diiodobenzene monomers at a loading ratio of 1:4 (biotinylated to non-biotinylated monomer) that were polymerized by a cross-coupling reaction with a diacetylene monomer. The mono-substituted biotinylated monomer used in the synthesis of polymer 1 was designed to provide binding accessibility for streptavidin while minimizing the divalent binding of one streptavidin onto the same repeat unit, if it were symmetrically functionalized with biotin. Polymers 3 and 4 were designed with a pentiptycene in the backbone to promote greater spectroscopic stability and biotin accessibility. Details of the synthesis of each of polymers 1-4 are further discussed below.

As an initial assay, biotinylated polymer 1 and control polymer 2 were each incubated with fluorescein-labeled streptavidin at room temperature (about 25° C.), in 50 mM Tris buffer at pH 7.4 for about five minutes. Fluorescein was selected as the streptavidin label, since its absorbance maximum at 490 nm partially overlaps with the emission maximum of polymer 1 at 486 nm. This selection also favors Förster ET between the polymer donor and dye acceptor upon binding of labeled streptavidin to biotin. When 0.030 nmol of labeled streptavidin was added to 2.16 nmol of polymer 1, an increase in the emission of the fluorescein was observed. The overlapping fluorescence spectra were deconvoluted to separate the emission of fluorescein from the emission of the polymer. Although the degree of enhancement in the fluorescence emission was generally low, these results indicate that biological recognition may be necessary for ET from the polymer to the dye-labeled streptavidin.

Figure 3F:
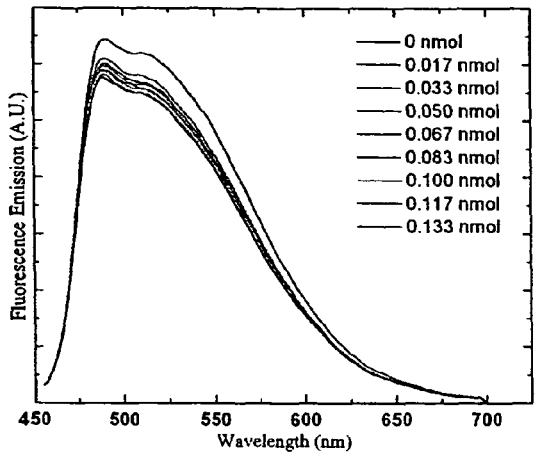
Figure 3G:
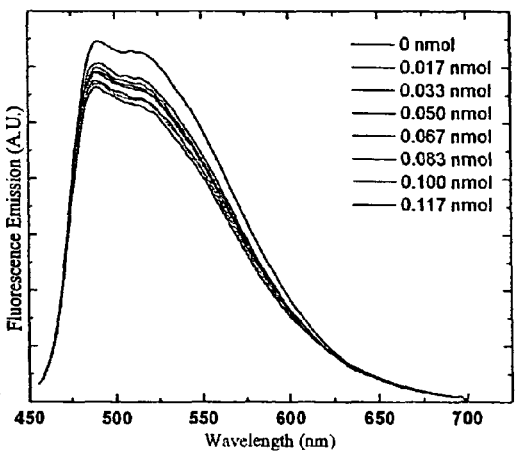
Figure 3H:
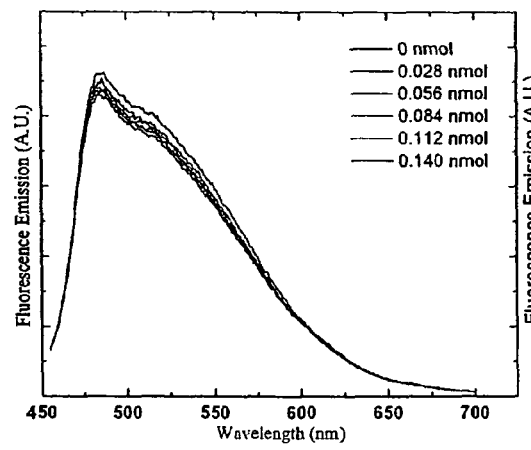
Figure 3I:
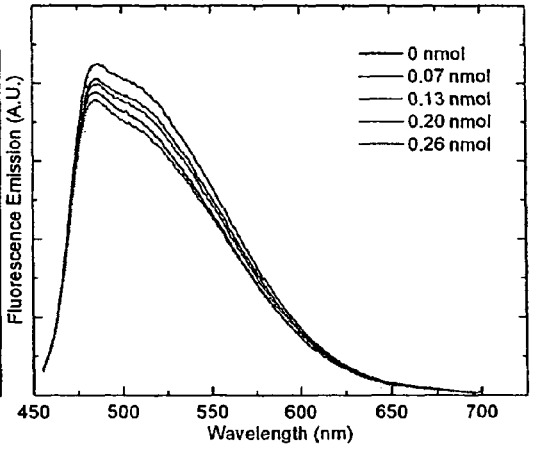

To better visualize ET between the polymer donor and the dye-acceptor, a more red-shifted label, rhodamine B-labeled streptavidin ("RhB-strept") (FIG. 3C) was used in the solution phase ET assays with polymer 1. Surprisingly, better ET was observed even though RhB had a diminished spectral overlap with polymer 1 (the emission maximum of polymer 1 was 486 nm, the absorption maximum of RhB-strept was 574 nm, at about 4.6 dyes/protein). Polymer 1 was then screened with Texas Red™ X-labeled streptavidin ("T-red-strept"), as shown in FIG. 3E. The absorption maximum was 591 nm, at about 2.9 dyes/protein. Remarkable ET was observed. Furthermore, these results were contrary to the Förster theory that governs FRET, where decreased spectral overlap results in diminished ET. Instead, for both dyes, the emission due to ET was amplified, compared to the direct excitation of the dyes at their absorbance maximum (see FIGS. 3A and 3B). In these figures, aliquots of 0.017 nmol of RhB-strept (FIG. 3A)

and T-red-strept (FIG. 3B) were added to 1.51 nmol of polymer 1. ET was observed in both cases, with amplified emission of dyes due to the light-harvesting conjugated polymers. The direct excitation of the dyes at 575 nm and 585 nm corresponded to 0.100 nmol of streptavidin. These results are consistent with the light-harvesting properties of conjugated polymers. These results also reveal that, in spite of their large differences in spectral overlap with polymer 1, both dyes appeared to give similar decreases in the polymer emissions. A control experiment with unlabeled streptavidin showed that this decrease was due to the presence of the dyes. Control experiments with polymer 2 showed no ET upon addition of both dye-labeled streptavidin derivatives. The addition of a biotin pre-saturated solution of T-red-strept to biotinylated polymer 1 was also performed. No decrease in fluorescence of the polymer, and no ET to the dye, were observed. Emission spectra for control experiments involving polymer 1 are illustrated in FIGS. 3F-3I. In these figures, FIG. 3F illustrates polymer 1 incubated with rhodamine red-labeled streptavidin, while FIG. 3G illustrates polymer 1 incubated with Texas Red™-X-labeled streptavidin, FIG. 3H illustrates polymer 1 incubated with biotin-saturated Texas Red™ X-labeled streptavidin, and FIG. 3I illustrates polymer 1 incubated with streptavidin.

The quantum yields of the streptavidin-bound dyes varied upon binding of polymer 1, which may be due to aggregation and/or an environmental change within the vicinity of the dyes with the polymer. This effect was observed by directly exciting the dyes at their maximum absorbance (where the polymer does not significantly absorb), using the same polymer concentrations as those described above with reference to FIGS. 3A and 3B. In the presence of polymer 1, the quantum yield of RhB-strept was diminished by about 38% while that of T-red decreased by about 63%. Nevertheless, greater emission intensity was observed for T-red-strept (FIG. 3B), despite the greater decrease in its quantum yield, as compared to RhB-strept. The strong emission response from T-red-strept therefore is probably not due to a simple improvement in its quantum efficiency.

Those results thus show that the ET from the polymer to the dyes may not be governed by Förster theory, and that an energy exchange mechanism, often referred to as Dexter Energy Transfer ("DET"), may be operative. This mechanism generally requires fairly close proximity between the donor and acceptor chromophores. To study these interactions, the Stern-Volmer ($K_{SV}$) quenching constants were determined from fluorescence emission and lifetime measurements in 50 mM Tris buffer at pH 7.4. Upon the addition of the streptavidin-free fluorescent dyes (fluorescein, RhB, and sulforhodamine 101, the Texas Red™ parent dye) to polymer 1, the apparent $K_{SV}$ values were determined to be 26,300 $M^{-1}$, 91,800 $M^{-1}$ and 97,900 $M^{-1}$, respectively. The bi-molecular quenching constant $k_q$ was found to range from $1.25 \times 10^{14}$ $M^{-1}s^{-1}$ to $3.4 \times 10^{14}$ $M^{-1}s^{-1}$ for the three dyes, which exceeded the diffusion constant and may be indicative of static quenching. The dyes therefore may have an inherent affinity for the conjugated polymer backbone. A more planar conformation and greater hydrophobic character for Texas Red™, compared to RhB and fluorescein, may permit better stacking and orbital interaction with the CP backbone, allowing for greater DET. In the case of dye-labeled streptavidin, biological recognition first may bring the dyes into closer proximity with the polymer. Conformational and hydrophobic characteristics of the dyes then may tailor the extent of orbital mixing with the polymer: the flatter Texas Red™ may interact more intimately with the planar conjugated polymer backbone then the other dyes. This may favor DET and can explain the better ET that was observed, even at decreased spectral overlap between the CP donor and dye acceptor.

Figure 4A:
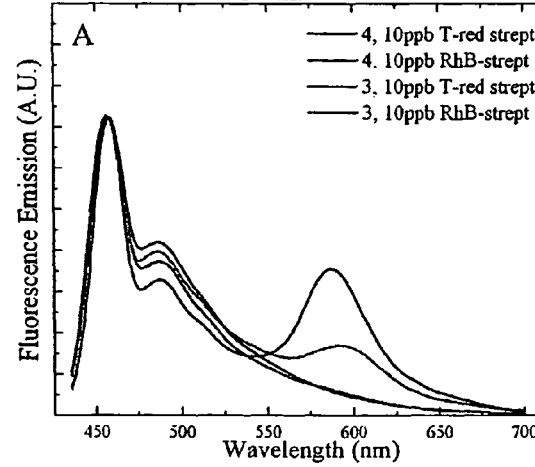
FIGS. 4A-4B illustrate spectral data according to an embodiment of the invention involving polymers in thin films.
Figure 4B:
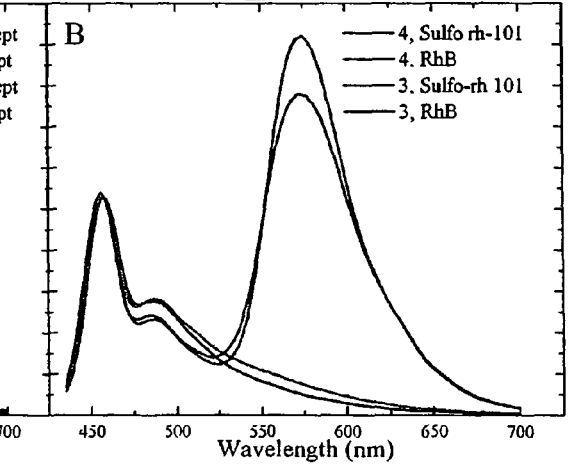

Thin film experiments with polymers 3 and 4 were also conducted in this example. Incubation with the dye-labeled streptavidin was performed in the presence of Triton X-100, a non-ionic detergent, to diminish non-specific binding. It was observed that RhB-strept exhibited better ET than T-red-strept (FIG. 4A). The spectra was scaled to 454 nm. However, a small "shoulder," due to non-specific binding, was observed when polymer 4 was incubated with RhB-strept. This finding suggests that the smaller RhB exhibits better orbital overlap with the more sterically restrictive structures of polymers 3 and 4. To verify the affinity of the free dyes with the conjugated polymers, the incubation of polymers 3 and 4 was carried out with the free dyes (FIG. 3B). Indeed, the free RhB dye associated with both 3 and 4, while free sulforhodamine 101 (Texas Red™) associated with neither (FIG. 3B). Thus, a more intimate interaction of the dyes with the polymer proved important for ET.

In summary, this example illustrates the design of a sensitive turn-on model biosensor based on ET between biotinylated polymer and a dye-labeled streptavidin. The mechanism is not solely a through space dipolar phenomenon typical of most FRET processes, but also may have a large electron exchange component.

In these experiments, polymers 1-4 were prepared as follows. In general, $^1H$ and $^{13}C$ NMR spectra for the monomers and the polymers were recorded on a Varian (300 MHz) or on a Varian VXR-500 (500 MHz) instrument. The chemical shift data for each signal are given in units of delta ($\delta$) (ppm) relative to tetramethylsilane (TMS) where delta ($\delta$) (TMS)=0, and referenced to the solvent residual. High-resolution mass spectra were obtained on a Finnigan MAT 8200 system using sector double focus and an electron impact source with an ionizing voltage of 70 V, and with a Bruker DALTONICS APEX II, 3 Tesla, FT-ICR-MS with ESI source or EI/CI source. UV-visible absorption spectra were measured with a Cary 50 UV/visible spectrometer. Fluorescence spectra were measured with a SPEX Fluorolog-2 fluorometer (model FL112, 450 W xenon lamp). The spectra in solution were obtained at room temperature using a quartz cuvette with a 1 cm path length. The polymer thin film spectra were recorded by front-face (22.5°) detection. Fluorescence quantum yields of polymers in Tris buffer (100 mM, pH 7.4) were determined relative to solutions of coumarin 6 (phi-F ($\Phi_F$)=0.78 in ethanol) as a reference. The quantum yields for solid state thin films were obtained relative to 0.01 mol % of 9,10-dipheynylanthracene in polymethylmethacrylate ("PMMA") (phi-F ($\Phi_F$)=0.83) as a reference. The molecular weights of polymers were determined by using three PLgel 5 mm $10^5$, $10^4$, $10^3$ (300×7.5 mm I.D) columns in series and a diode detector at 254 nm at a flow rate of 1.0 ml/min in tetrahydrofuran ("THF") or in dimethylformamide ("DMF"). The molecular weights were reported relative to polystyrene or poly(ethylene oxide) standards purchased from Agilent Inc. Polymer thin films on a cover glass (18×18 mm, pretreated with 1,1,1,3,3,3-hexamethyldisilazane) were spin cast on an EC101DT photoresist spinner (Headway Research Inc.) using a spin rate of 3000 rpm from a chloroform solution. Melting points (m.p.) were determined using a Laboratory. Devices MEL-TEMP instrument (open capillaries used) and were uncorrected.

All solvents were spectral grade unless otherwise noted. Morpholine and biotin were purchased from Alfa Aesar and used as received. Fluorescein conjugated streptavidin, rhodamine-conjugated streptavidin, Texas Red™ X conjugated streptavidin and sulforhodamine 101 were purchased from Molecular Probes Inc. and used as received. All other chemicals were purchased from Aldrich Chemical Inc. and used as received. All air and water sensitive synthetic manipulations were performed under a nitrogen atmosphere using standard Schlenk techniques.

Figure 5A:
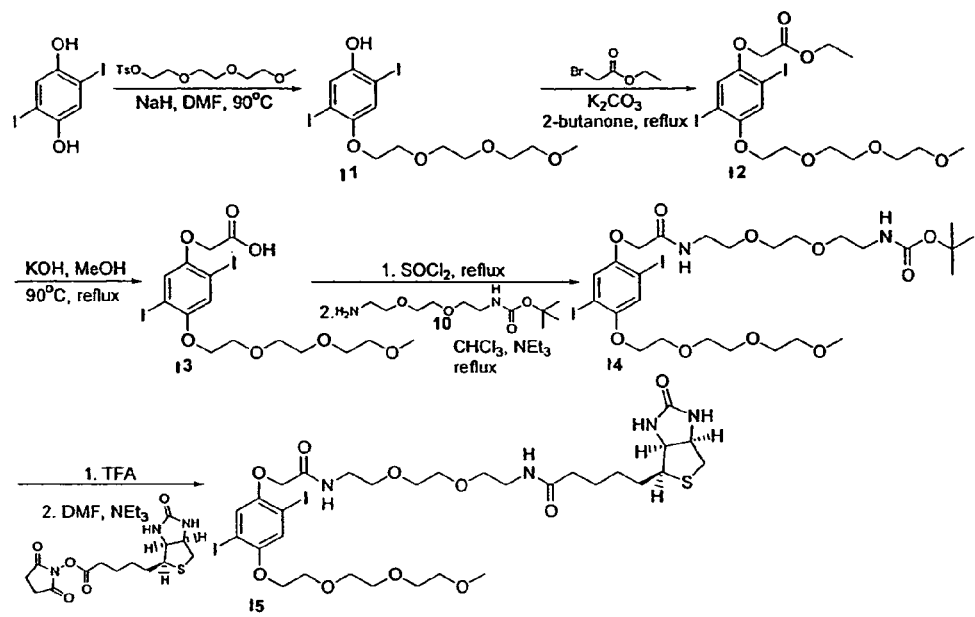

Monomer 15 was prepared according to the scheme shown in FIG. 5A as follows. To a 250 ml round bottom flask equipped with a reflux condenser containing 2,5-diiodo-1,4-dihydroxybenzene (10.00 g, 27.6 mmol) was added 125 ml anhydrous N,N'-dimethylformamide ("DMF") under nitrogen. The solution was cooled to 0° C., and nitrogen was bubbled through the solution for 15 minutes. NaH as a 60% dispersion in mineral oil (1.326 g, 33.2 mmol) was added and the resulting suspension was stirred for 20 min at 0° C. Triethylene glycol monomethyl ether p-toluenesulfonate (9.94 g, 31.2 mmol) was then transferred to the solution via syringe. The reaction was heated at 65° C. for 14 h under nitrogen. A light clear brown solution was obtained. DMF was removed under reduced pressure and the resulting brown oil was extracted with ethyl acetate (500 ml total) against 200 ml $H_2O$. The organic layer was washed with 50 ml brine and the solvent was removed under reduced pressure. The product was purified by column chromatography with 6:4 hexane/ethyl acetate to afford a colorless oil which solidified to a white solid upon standing (3.98 g, 28%). m.p. 81-83° C. $^1$H NMR (300 MHz, $CDCl_3$): 7.38 (1H, s), 7.09 (1H, s), 5.27 (1H, s), 4.08 (2H, t, J=4.5 Hz), 3.88 (2H, t, J=4.5 Hz), 3.79 (2H, t, J=4.5 Hz), 3.69 (2H, t, J=4.5 Hz), 3.67 (2H, t, J=4.5 Hz), 3.38 (3H, s); $^{13}$C NMR (125 MHz, $CDCl_3$): 152.6, 150.5, 125.0, 121.9, 87.8, 84.4, 72.1, 71.3, 71.0, 70.8, 70.5, 69.8, 59.3; HR-MS (EI) calcd. for $C_{13}H_{18}I_2O_5$ (M+): 507.9238. found: 507.9239.

In a 250 ml round bottom flask were combined molecule 11 (2.00 g, 3.94 mmol), $K_2CO_3$ (1.632 g, 11.81 mmol), ethyl bromoacetate (0.567 ml, 5.12 mmol) and 100 ml acetone. The flask was fitted with a reflux condenser and the reaction mixture was refluxed for 12 h. A pale yellow suspension resulted. This was cooled, filtered and the solvent was removed under reduced pressure. The residue was purified by column chromatography with 6:4 hexane/ethyl acetate, and the product was isolated as a colorless oil which solidified upon standing to a white solid (2.02 g, 86%). m.p. 44-45° C. $^1$H NMR (300 MHz, $CDCl_3$): 7.26 (1H, s), 7.17 (1H, s), 4.61 (2H, s), 4.30 (2H, q, J=4.2), 4.13 (2H, t, J=3 Hz), 3.88 (2H, t, J=3 Hz), 3.80 (2H, t, J=3 Hz), 3.70 (2H, t, J=3 Hz), 3.68 (2H, t, J=3 Hz), 3.57 (2H, t, J=3 Hz), 3.39 (3H, s), 1.32 (3H, t, J=4.2 Hz); $^{13}$C NMR (125 MHz, $CDCl_3$): 168.4, 153.9, 152.4, 123.9, 123.6, 86.7, 86.4, 72.2, 71.4, 71.0, 70.8, 70.4, 69.8, 67.7, 61.7, 59.3, 14.5. HR-MS (EI) calcd. for $C_{17}H_{24}I_2O_7$ (M+): 593.9606. found: 593.9625.

In a 250 ml round bottom flask were combined molecule 12 (2.00 g, 3.36 mmol) and KOH (0.944 g, 16.8 mmol) in 70 ml methanol. A reflux condenser was fitted and the reaction was heated to reflux for 14 h. The solvent was removed under reduced pressure. 45 ml 10% $HCl_{(aq)}$ was added. The product precipitated and was isolated by centrifugation followed by lyophilization. A white solid was obtained (1.79 g, 94%). m.p. 74-76° C. $^1$H NMR (300 MHz, DMSO): 7.38 (1H, s), 7.24 (1H, s), 4.72 (2H, s), 4.10 (2H, t, J=4.5 Hz), 3.73 (2H, t, J=4.5 Hz), 3.62 (2H, t, J=4.5 Hz), 3.5 (2H, t, J=4.5 Hz), 3.52 (2H, t, J=4.5 Hz), 3.42 (2H, t, J=4.5 Hz), 3.23 (3H, s); $^{13}$C NMR (125 MHz, DMSO): 169.8, 152.7, 151.7, 123.0, 122.2, 86.7, 86.5, 71.3, 70.2, 69.9, 69.7, 69.6, 69.0, 66.1, 58.0; HR-MS (ESI) calcd. For $C_{15}H_{20}I_2O_7$ (M+Na): 588.9191. found: 588.9182.

In a 50 ml round bottom flask equipped with a reflux condenser containing molecule 13 (0.500 g, 0.883 mmol) was added 5 ml $SOCl_2$. This was refluxed for 10 h. The thionyl chloride was then removed under reduced pressure to afford the acid chloride as a pale yellow oil (0.521 g, 0.883 mmol). To this was then added 20 ml $CH_2Cl_2$. Anhydrous $NEt_3$ was then added (0.185 ml, 1.32 mmol) and the mixture was stirred for 5 min. Molecule 10 (0.329 g, 1.32 mmol) was added as a solution in 10 ml $CH_2Cl_2$. The reaction mixture was refluxed for 12 h. The solvent was removed under reduced pressure. The residue was dissolved in 100 ml $CHCl_3$ and washed with 30 ml $H_2O$. The organic layer was washed with 15 ml brine, dried over $MgSO_4$. The organic solvent was removed under reduced pressure to afford a colorless oil which solidified upon standing to a white solid (0.560 g, 80%). m.p. 81-83° C. $^1$H NMR (300 MHz, $CDCl_3$): 7.28 (1H, br), 7.25 (1H, s), 7.17 (1H, s), 4.90 (1H, br), 4.13 (2H, t, J=4.5 Hz), 3.90 (2H, t, J=4.5 Hz), 3.80 (2H, t, J=4.5 Hz), 3.81-3.52 (16H, m), 3.39 (3H, s), 3.32 (2H, t, J=5.1 Hz), 1.45 (9H, s); $^{13}$C NMR (125 MHz, $CDCl_3$): 206.1, 167.4, 156.2, 154.1, 151.4, 123.3, 86.8, 86.3, 79.5, 72.2, 71.4, 71.0, 70.8, 70.6, 70.6, 70.5, 70.0, 69.8, 69.1, 59.3, 40.5, 39.1, 28.7; HR-MS (ESI) calcd. for $C_{26}H_{42}I_2N_2O_{10}$ (M+H): 797.1002. found: 797.1022.

A 50 ml round bottom flask containing molecule 14 (0.487 g, 0.611 mmol) was loaded with 2 ml trifluoroacetic acid ("TFA"). The clear yellow solution was stirred for 30 min. The TFA was removed, 2 ml $H_2O$ was added and was also removed under reduced pressure. The deprotected product was dried under high vacuum. To this was added 5 ml anhydrous DMF, $NEt_3$ (0.450 ml, 3.22 mmol). This was stirred for 15 min, then N-hydroxysuccinimidobiotin (0.212 g, 0.624 mmol) was added. The pale yellow solution quickly became a thick white slurry and was stirred at room temperature for 40 h. The solvent was removed under reduced pressure at 40° C. and the reaction mixture was washed with 25 ml $H_2O$. The product was isolated by centrifugation and lyophilized to afford a white powder (0.525 g, 94%). m.p. 175-176° C. $^1$H NMR (500 MHz, $CDCl_3$): 7.85 (2H, m), 7.39 (1H, s), 7.31 (1H, s), 6.43 (1H, s), 6.36 (1H, s), 4.52 (2H, s) 4.30 (1H, m), 4.11 (1H, m), 3.74 (2H, t, J=5.0 Hz), 3.62 (2H, t, J=5.0 Hz), 3.54-3.30 (16H, m), 3.22 (3H, s), 3.18 (2H, m), 3.08 (2H, m), 2.80 (1H, dd, J=12.5, 5.0 Hz), 2.58 (J=12.5 Hz), 2.06 (2H, t, J=7.5 Hz), 1.62-1.57 (1H, m), 1.52-1.43 (3H, m), 1.32-1.26 (2H, m); $^{13}$C NMR (125 MHz, $CDCl_3$): 172.1, 167.2, 162.7, 153.0, 151.7, 123.3, 122.7, 86.9, 86.8, 71.3, 70.2, 69.9, 69.7, 69.2, 69.0, 68.8, 61.3, 61.0, 59.2, 58.1, 55.5, 38.44, 30.37, 35.1, 28.2, 28.1, 25.3; HR-MS (ESI) calcd. for $C_{31}H_{48}I_2N_4O_{10}S$ (M+H): 923.1253. found: 923.1210.

Polymer 1 was prepared as is shown schematically in FIG. 5B. A 25 ml Schlenk flask was charged with molecules 15 (0.0205 g, 0.022 mmol), 16 (0.0606 g, 0.089 mmol) and 17 (0.050 g, 0.111 mmol), $Pd(PPh_3)_4$ (6.41 mg, 0.0056 mmol) and CuI (1.06 mg, 0.0056 mmol) under $N_2$. To this was added 1.5 ml freshly degassed morpholine under $N_2$. The reaction vessel was sealed and heated at 60° C. for 48 h. 3 ml $H_2O$ was added and the reaction mixture was dialyzed (cellulose membrane, MWCO 10,000) against 1 L deionized water for 2 days (6 water changes). The polymer was then lyophilized to afford an orange polymer (97 mg, 95%). $M_n$=130,000, PDI=1.48 for DMF soluble fraction. $^1$H NMR (500 MHz, DMF): 7.29 (20H, br), 6.39 (1H, s), 6.32 (1H, s), 4.78 (2H, s), 4.33 (38H, br), 3.94 (24H, br), 3.78-3.46 (160H, broad multiplet), 3.28 (33H, br), 1.60 (8H, br).

Figure 5C:
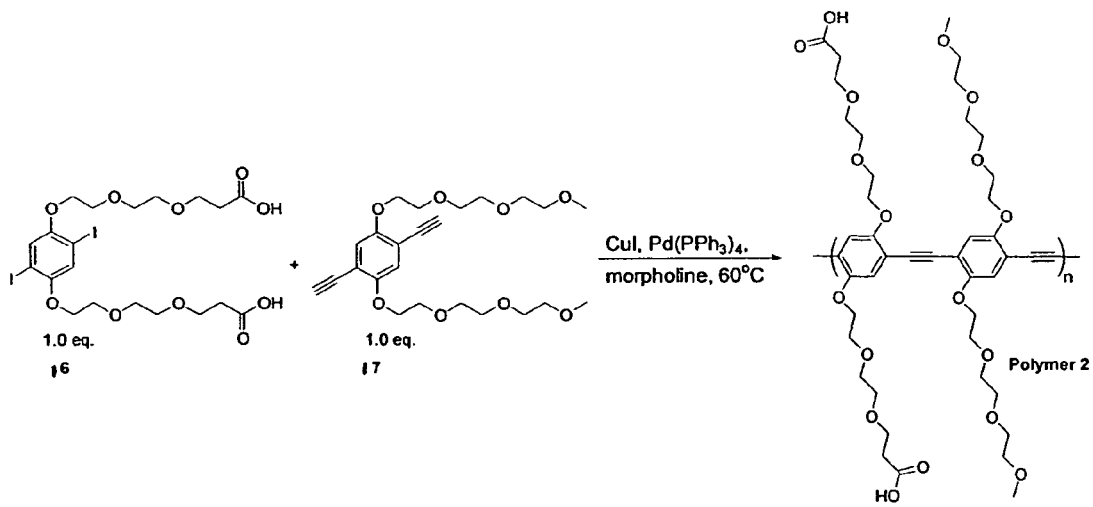

Polymer 2 was prepared as is shown schematically in FIG. 5C. A 25 ml Schlenk flask was charged with molecules 16 (0.0454 g, 0.066 mmol) and 17 (0.030 g, 0.066 mmol), $Pd(PPh_3)_4$ (3.85 mg, 0.00333 mmol) and CuI (0.634 g, 0.00333 mmol) under $N_2$. To this was added 1.0 ml freshly degassed morpholine under $N_2$. the reaction vessel was then sealed and heated at 60° C. for 48 h. 3 ml H$_2$O was added and the mixture was dialyzed against 1 L deionized water for 2 days (6 water changes). It was then lyophilized to afford an orange polymer (56 mg, 96%). M$_n$=128,000, PDI=1.53 for DMF soluble fraction. $^1$H NMR (500 MHz, DMF): 7.30 (4H, s), 4.34 (8H, br), 3.95 (8H, br), 3.79-3.46 (32H, br), 3.29 (6H, s)

Polymer 3 was prepared as is shown schematically in FIG. 5D. A 25 ml Schlenk flask was charged with molecules 15 (0.00796 g, 0.00819 mmol), 18 (0.0214 g, 0.0328 mmol), and 19 (0.020 g, 0.418 mmol), Pd(PPh$_3$)$_4$ (2.367 mg, 0.00205 mmol), and CuI (0.390 mg, 0.00205 mmol) under N$_2$. 1.5 ml of a freshly degassed mixture of 4:1 toluene/diisopropylamine, and 0.5 ml freshly degassed DMF were added via syringe. The reaction vessel was sealed and heated at 60° C. for 5 days. The polymer was isolated by precipitation into methanol followed by centrifugation. A yellow powder was obtained (32 mg, 83%). M$_n$=7,700, PDI=2.04 for THF soluble fraction. $^1$H NMR (500 MHz, CDCl$_3$): 7.66-7.47 (60H, broad multiplet), 7.05 (40H, br), 6.42 (1H, s), 6.39 (1H, s), 6.10 (20H, br), 5.30 (2H, br), 4.68 (20H, br), 4.26 (22H, br), 3.83 (20H, br), 3.65 (20H, br), 3.55 (20H, br), 3.44 (20H, br), 3.31 (19H, br), 2.78 (2H), 1.40-1.25 (6H, broad multiplet).

Figure 5E:
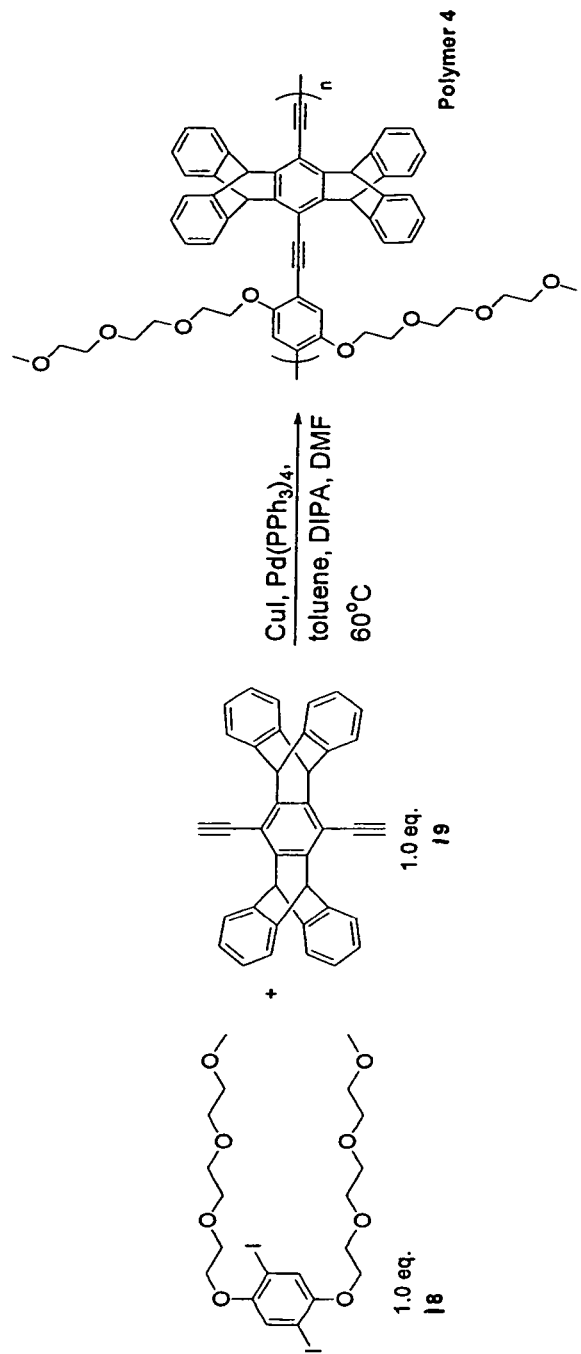

Polymer 4 was prepared as is shown schematically in FIG. 5E. A 25 ml Schlenk flask was charged with molecules 18 (0.020 g, 0.0306 mmol) and 19 (0.0149 g, 0.0312 mmol), Pd(PPh$_3$)$_4$ (1.766 mg, 0.00153 mmol) and CuI (0.291 mg, 0.00153 mmol) under N$_2$. 1.5 ml of a freshly degassed mixture of 4:1 toluene/diisopropylamine was added via syringe. The reaction vessel was sealed and heated at 60° C. for 5 days. The polymer was isolated by precipitation into ethyl acetate followed by centrifugation. A yellow powder was obtained (21.3 mg, 80%). M$_n$=14,000, PDI=2.02 for THF soluble fraction. $^1$H NMR (500 MHz, CDCl$_3$): 7.53 (10H, broad multiplet), 7.05 (8H, br), 6.20 (4H, br), 4.68 (4H, br), 4.26 (4H, br), 3.82 (4H, br), 3.65 (4H, br), 3.55 (4H, br), 3.44 (4H, br), 3.31 (6H, br).

To perform energy transfer assays in the solution phase, the following general protocol was used. 7.5 microliters of a stock polymer solution (1 mg/ml in Tris buffer, 40 mM at pH 7.4) was diluted with the same Tris buffer to a total volume of 3 ml in a fluorescence cuvette. To this was added aliquots of dye-labeled streptavidin (1 microliter of a 1 mg/ml solution) and the fluorescence emission was taken at each addition. The excitation wavelength at 440 nm was chosen, and emission spectrum was taken from 455 nm-700 nm.

To perform energy transfer assays in solid phase, the following general protocol was used. The microscope coverslips were pretreated in 1,1,1,3,3,3-hexamethyldisilazane. The polymer solutions at 1 mg/ml in chloroform were spin-cast onto microscope coverslips at a spin rate of 3000 rpm for 1 minute. The coverslips were put under vacuum for 2 h, then were incubated in a solution of dye labeled streptavidin or dye for 1 h. The coverslips were then washed with deionized water, blotted dry and dried under vacuum for a minimum of 5 h. The excitation wavelength at 400 nm was chosen, and the emission spectrum was taken from 415 nm-700 nm.

Example 2

Figure 6:
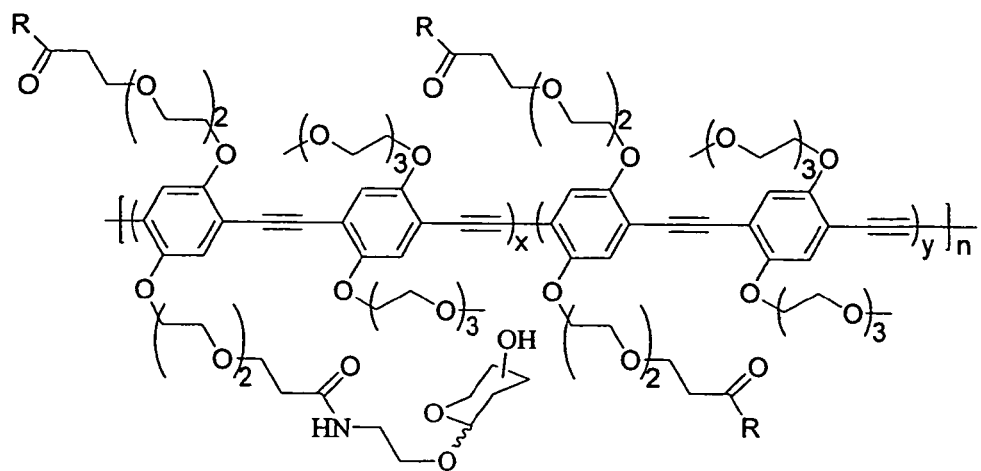
FIG. 6 illustrates certain polymers in accordance with another embodiment of the invention.

This example illustrates a carbohydrate functionalized poly(p-phenylene ethynylene) ("PPE") that can be used for detection of *E. coli* by multivalent interactions. This polymer is functionalized after polymerization and provides a versatile scaffold for the rapid attachment of a variety of different carbohydrates (FIG. 6).

Coupling of the 2-aminoethyl mannoside and galactoside1 to the PPE was carried out in the presence of 1-ethyl-3-(3-dimethylaminopropyl)-carbodiimide ("EDAC") and N,N'-diisopropylethylamine for 16-24 h. This was followed by quenching of unreacted succinimide esters via addition of excess ethanolamine. Uncoupled reagents were removed by dialysis of the reaction mixture against water for 2 days. A phenol sulfuric acid test for carbohydrate loading showed that typically 25% of the reactive sites on the polymer were functionalized with glycosides.

To insure that the mannose moieties conjugated to the polymer retained their ability to interact with carbohydrate binding lectins, a fluorescence resonance energy transfer ("FRET") experiment was carried out between Alexa Fluor 594™ labeled concanavalin A ("Con A," a mannose binding protein) and each of the sugar-functionalized PPEs. Titration of labeled Con A into a solution of mannose coated polymer showed a concentration dependent decrease in fluorescence signal. In contrast, experiments with galactose coated polymer showed no fluorescence change, as expected. Thus, mannose binding lectins interacted with mannose displayed on the polymer and selectivity was retained. Furthermore, the polymer did not exhibit any non-specific binding to Con A.

Two bacterial strains that differed only in their mannose binding properties were used to assess whether the mannosylated PPE 22a could fluorescently stain *E. coli*. In addition to a strain that binds to mannose, a second strain that is mutated in its mannose binding protein (FimH) to abolish mannose binding was used. The non-functionalized polymer 21, the mannosylated polymer 22a, and 2'-fluorescein aminoethyl mannoside were individually incubated with these bacterial strains. After incubating a 1 ml bacterial suspension at an OD600 of 1.0 with the appropriate polymer or dye labeled mannose for 30 minutes, the suspensions were centrifuged to pellet the cells. The supernatant solution containing unbound polymer or dye labeled mannose was discarded and the cells were washed twice with phosphate buffered saline (PBS, pH 7.2). The bacteria were then resuspended in PBS. Neither polymer 21 nor the 2'-fluorescein aminoethyl mannoside appeared to bind either *E. coli* strain. The mannosylated polymer 22a, however, imparted a strong fluorescent label to wild type *E. coli* (FIG. 7) that was not removed even upon separation and rinsing. The resuspended rinsed non-mannose binding *E. coli* gave no polymer fluorescence after incubation with polymer 22a.

Figure 7:
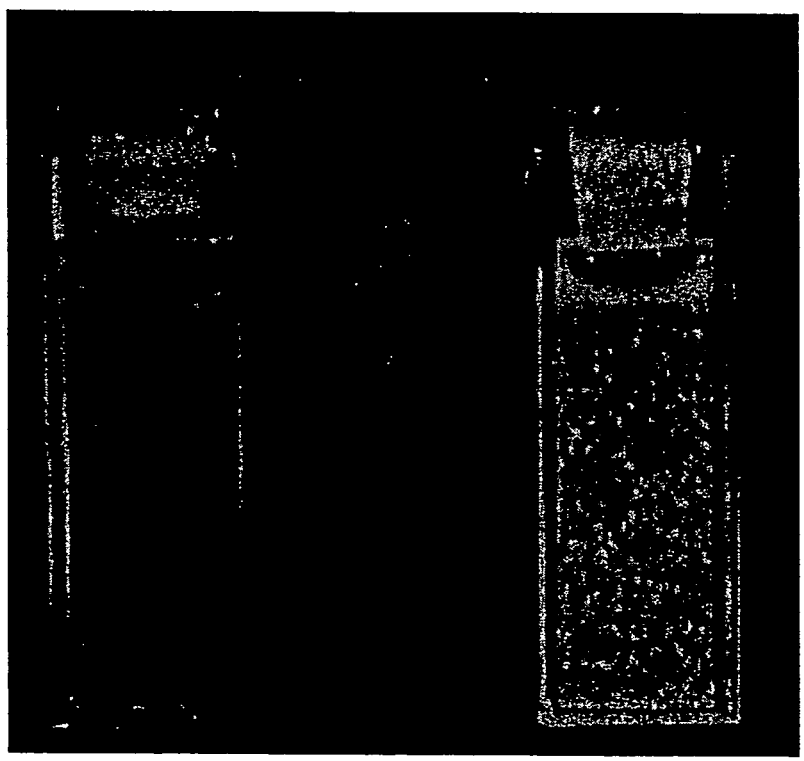
FIG. 7 is a photomicrograph illustrating the fluorescence of certain bacteria, as determined using an embodiment of the invention.

FIG. 7 illustrates the visualization of mutant (left) and mannose binding (right) *E. coli* strains after incubation with mannosylated polymer 22a with a transillumiator. Approximately 10 micrograms of polymer was incubated with 1.0 OD600 of cells. The cells were imaged under a transilluminator.

These results suggest that multivalent interactions may be critical for detection, since the mannosylated PPE allowed for fluorescent detection of *E. coli* while 2'-fluorescein aminoethyl mannoside did not. The multivalent binding nature of polymer 22a was demonstrated by testing this polymer for hemagglutination inhibition of sheep erythrocytes (Table 1). The inhibition values were found to be over 500-fold greater for the polymer compared to the monomeric mannose derivatives.

TABLE 1

| COMPOUND | INHIBITING DOSE, M |
|---|---|
| Mannose | 0.02 |
| 2'-Aminoethyl mannoside | 0.01 |

TABLE 1-continued

| COMPOUND | INHIBITING DOSE, M |
|---|---|
| 2'-Fluorescein aminoethyl mannoside | 0.01 |
| Mannose conjugated polymer 22a | $16 \times 10^{-6}$ |
| Non-functionalized polymer 21 | N.D. |

Binding of mannosylated polymer to bacteria was imaged using laser scanning confocal microscopy and fluorescence microscopy. After incubation with polymer 22a, the mutant bacteria remained as individual cells that did not bind to polymer (FIG. 8A), while the wild type bacteria formed clusters with fluorescent centers where the polymer was bound to many cells (FIG. 8B). These brightly fluorescent clusters were formed by thirty to several thousand bacteria (FIGS. 8B and 8C). The larger clusters had the strongest fluorescence signal while single cells in the culture exhibited little fluorescence. Such direct polymer-cell clustering has not been previously reported with E. coli, nor has it been used for detection purposes. Additionally, the fluorescence emission spectrum of the polymer in the bacterial clusters exhibited a more red-shifted and aggregated behavior (increased emission at 550 nm) than spectra in PBS solution (FIG. 8D). This is consistent with increased pi-stacking interactions between the polymer strands as they are brought into closer proximity by the bacteria.

FIGS. 8A-8B illustrate laser scanning confocal microscopy images. FIG. 8A illustrates mutant type E. coli that did not bind to polymer 22a. Individual cells were observed with no aggregation. FIG. 8B shows fluorescent bacterial aggregate due to multivalent interactions between the wild type bacterial pili and polymer 22a (superimposed fluorescence and transmitted light images). FIG. 8C shows a fluorescence microscopy image of a large fluorescent bacterial cluster. FIG. 8D is a conventional fluorescence spectra of polymer 22a in PBS (solid line) and normalized fluorescence spectra of a bacterial cluster obtained using confocal microscopy (dotted line).

In conclusion, a new method for fluorescent detection of bacteria based on water soluble fluorescent conjugated polymers has been illustrated in this example. Glycosides displayed on the surface of the polymers retained their ability to interact with known carbohydrate binding lectins. Incubation of the polymers with E. coli showed that the polymers were able to bind to bacteria and yield brightly fluorescent cell clusters. This aggregation may be due to multivalent interactions between the mannosylated polymer and mannose receptors located on the bacterial pili, which was supported by microscopy and hemagglutination experiments. This multivalency and resulting cell aggregation can be essential for detection. The preference of different bacteria to bind to specific carbohydrates may allow the potential sensing of a range of pathogens, such as cholera, in water and other sources.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of determining a biological entity, comprising: exposing a sample suspected of containing a biological entity to at least two fluorescent pi-conjugated polymers, each polymer comprising a phenylene ethynylene backbone having at least two phenylene ethynylene groups and a plurality of biological recognition elements covalently attached to the pi-conjugated polymer via the phenyl groups of the phenylene ethynylene backbone, wherein the biological recognition elements are able to specifically interact with the biological entity;
    allowing the biological entity, if present, to interact with the biological recognition elements of the at least two fluorescent pi-conjugated polymers in a manner bringing said at least two fluorescent pi-conjugated polymer into proximity with each other such that an emissive signal is produced at a threshold level;
    and determining fluorescence of the sample.

2. The method of claim 1, wherein the at least two fluorescent pi-conjugated polymers have the same chemical structure.

3. The method of claim 1, wherein the biological recognition elements are carbohydrates, glycosaminoglycans, glycolipids, proteins, antibodies, glycoproteins, lectins, or nucleic acids.

4. The method of claim 3, wherein the carbohydrates are monosaccharides, oligosaccharides, or polysaccharides.

5. The method of claim 3, wherein the carbohydrates are mannose, fucose, sialic acid, heparin, or the Lewis group antigens.

6. The method of claim 1, wherein the biological entity is a bacterium, a virus, or a protein.

7. The method of claim 1, wherein the biological entity is a cell surface receptor or an enzyme.

8. The method of claim 1, wherein the biological entity is a *Escherichia coli*, *Salmonella entrica*, *Psuedomonas aerginosa*, influenza virus, herpes simplex virus, or *Helicobacter pylori*.

9. The method of claim 1, wherein the pi-conjugated polymer comprises the structure,

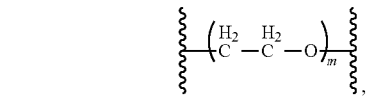

wherein:
n is greater than 1,
A and C can be the same or different and are a phenyl group, a triptycene group, or a pentiptycene group;
B and D are carbon-carbon triple bonds;
L is a moiety connecting A to R; and
R is a biological recognition element.

10. The method of claim 9, wherein:
A is a phenyl group;
C is a phenyl group, a triptycene group, or a pentiptycene group;
R is a carbohydrate; and
L is a moiety comprising —CO—NH—, —(CH$_2$)$_p$—, wherein p is at least 1, —NH—CH$_2$—CH$_2$—, —CH$_2$—CH$_2$—CO—, —CH$_2$—CH$_2$—CO—NH—CH$_2$—CH$_2$—, —O—CH$_2$—CO—NH—, —CH$_2$—CH$_2$—NH—, or

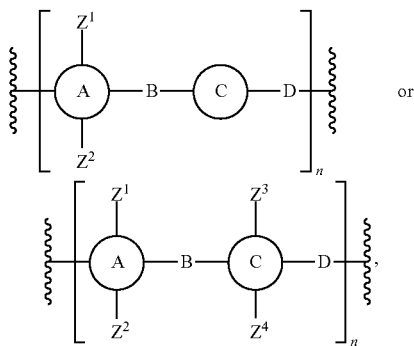

where m is at least 1.

11. The method of claim 1, wherein the pi-conjugated polymer comprises the structure, wherein:
n is greater than 1,
A and C can be the same or different and are a phenyl group, a triptycene group, or a pentiptycene group;
B and D are carbon-carbon triple bonds;
Z$^1$, Z$^2$, Z$^3$, and Z$^4$ can be the same or different and are groups comprising an ethylene glycol moiety, provided that at least one of Z$^1$, Z$^2$, Z$^3$, and Z$^4$ further comprises a biological recognition element.

12. The method as in claim 11, wherein the biological recognition element is mannose.

13. The method as in claim 11, wherein the biological recognition element is galactose.

* * * * *